(12) United States Patent
Geffen et al.

(10) Patent No.: US 8,975,251 B2
(45) Date of Patent: Mar. 10, 2015

(54) METHODS OF IMPROVING COGNITIVE FUNCTIONS

(75) Inventors: Yona Geffen, Doar-Na Lachish Tzafon-Moshav Nir Banim (IL); Kinneret Savitsky, Tel-Aviv (IL); Abraham Nudelman, Rechovot (IL); Ada Rephaeli, Herzlia (IL); Irit Gil-Ad, Herzlia (IL); Abraham Weizman, Tel-Aviv (IL)

(73) Assignees: Bar-Ilan University, Ramat-Gan (IL); Ramot at Tel-Aviv University Ltd., Tel-Aviv (IL)

(*) Notice: Subject to any disclaimer, the term of this patent is extended or adjusted under 35 U.S.C. 154(b) by 642 days.

(21) Appl. No.: 12/963,959

(22) Filed: Dec. 9, 2010

(65) Prior Publication Data

US 2011/0178073 A1 Jul. 21, 2011

Related U.S. Application Data

(60) Provisional application No. 61/267,883, filed on Dec. 9, 2009.

(51) Int. Cl.
*A61K 31/54* (2006.01)
*C07D 279/26* (2006.01)
*A61K 31/5415* (2006.01)

(52) U.S. Cl.
CPC .......... *C07D 279/26* (2013.01); *A61K 31/5415* (2013.01)
USPC ...................................................... 514/225.8

(58) Field of Classification Search
None
See application file for complete search history.

(56) References Cited

U.S. PATENT DOCUMENTS

| | | | |
|---|---|---|---|
| 2,914,528 A | 11/1959 | Craig | |
| 2,944,053 A | 7/1960 | Edgerton | |
| 2,969,358 A | 1/1961 | Cusic | |
| 3,227,708 A | 1/1966 | Yale et al. | |
| 3,956,493 A | 5/1976 | Yale | |
| 3,966,930 A | 6/1976 | Buus et al. | |
| 3,978,216 A | 8/1976 | Fuxe | |
| 4,153,694 A | 5/1979 | Buus et al. | |
| 4,629,691 A | 12/1986 | Collins et al. | |
| 4,818,936 A | 4/1989 | Kemlo | |
| 5,051,448 A | 9/1991 | Shashoua | |
| 5,104,858 A | 4/1992 | Hait et al. | |
| 5,145,684 A | 9/1992 | Liversidge et al. | |
| 5,525,727 A | 6/1996 | Bodor | |
| 5,828,405 A | 10/1998 | Vanier et al. | |
| 5,966,673 A | 10/1999 | Shannon | |
| 5,983,238 A | 11/1999 | Becker et al. | |
| 5,994,392 A | 11/1999 | Shashoua et al. | |
| 6,020,954 A | 2/2000 | Aggarwal | |
| 6,121,325 A | 9/2000 | Chen et al. | |
| 6,197,764 B1 | 3/2001 | Bradley et al. | |
| 6,239,867 B1 | 5/2001 | Aggarwal | |
| 6,294,562 B1 | 9/2001 | Stilz et al. | |
| 6,304,853 B1 | 10/2001 | Malnekoff | |
| 6,381,510 B1 | 4/2002 | Amidhozour et al. | |
| 6,569,853 B1 | 5/2003 | Borisy et al. | |
| 7,544,681 B2 | 6/2009 | Nudelman et al. | |
| 7,598,239 B2 | 10/2009 | Nudelman et al. | |
| 7,619,006 B2 | 11/2009 | Nudelman et al. | |
| 7,939,525 B2 | 5/2011 | Nudelman et al. | |
| 2001/0024532 A1 | 9/2001 | Malnekoff | |
| 2002/0010208 A1 | 1/2002 | Shashoua et al. | |
| 2002/0021439 A1 | 2/2002 | Priestley et al. | |
| 2002/0052170 A1 | 5/2002 | Holloway | |
| 2003/0065586 A1 | 4/2003 | Shaftel et al. | |
| 2003/0115079 A1 | 6/2003 | Rapaport | |
| 2004/0068417 A1 | 4/2004 | Sevdermish | |
| 2004/0103447 A1* | 5/2004 | Nawa et al. ........................ 800/9 |
| 2004/0242570 A1 | 12/2004 | Nudelman et al. | |
| 2005/0149369 A1 | 7/2005 | Sevdermish | |
| 2006/0046967 A1 | 3/2006 | Satyam | |
| 2006/0058219 A1 | 3/2006 | Miller | |
| 2006/0142181 A1 | 6/2006 | Miller | |
| 2007/0099977 A1 | 5/2007 | Nudelman et al. | |
| 2007/0197514 A1 | 8/2007 | Nudelman et al. | |
| 2007/0219181 A1 | 9/2007 | Kimura et al. | |
| 2008/0108606 A1 | 5/2008 | Nudelman et al. | |
| 2009/0215809 A1 | 8/2009 | Yao et al. | |
| 2009/0298814 A1 | 12/2009 | Nudelman et al. | |
| 2009/0304584 A1 | 12/2009 | Nudelman et al. | |
| 2010/0063034 A1 | 3/2010 | Nudelman et al. | |
| 2010/0120755 A1 | 5/2010 | Nudelman et al. | |
| 2010/0204469 A1 | 8/2010 | Nudelman et al. | |
| 2011/0312948 A1 | 12/2011 | Nudelman et al. | |
| 2013/0184347 A1 | 7/2013 | Nudelman et al. | |

FOREIGN PATENT DOCUMENTS

| | | |
|---|---|---|
| CA | 2461663 | 4/2003 |
| CN | 1596141 | 3/2005 |
| CN | 1997400 | 7/2007 |
| EP | 0361485 | 4/1990 |
| ES | 8707175 | 10/1987 |
| GB | 829246 | 3/1960 |
| GB | 1460713 | 5/1978 |
| GB | 1514312 | 6/1978 |
| GB | 2159636 | 12/1985 |
| GB | 2188630 | 10/1987 |

(Continued)

OTHER PUBLICATIONS

Nudelman et al., J. Med. Chem., Oct. 2, 2007, 51, 2858-2862.*

(Continued)

*Primary Examiner* — Dennis Heyer
*Assistant Examiner* — Daniel M Podgorski

(57) ABSTRACT

Methods and articles of manufacture for use in improving a cognitive function, utilizing a conjugate comprising a first moiety having GABA agonist activity and a second moiety having CNS activity being covalently linked to the first moiety, are disclosed. Also disclosed are methods and articles of manufacture of preventing onset or inhibiting progression of a cognitive impairment or dysfunction utilizing the disclosed conjugate.

9 Claims, 5 Drawing Sheets

(56) References Cited

FOREIGN PATENT DOCUMENTS

| | | |
|---|---|---|
| GB | 2358541 | 7/2001 |
| IL | 161083 | 9/2002 |
| IL | 199877 | 9/2002 |
| JP | 50-025574 | 3/1975 |
| JP | 53-050185 | 5/1978 |
| JP | 62-501991 | 8/1987 |
| JP | 62-240660 | 10/1987 |
| JP | 02-128564 | 5/1990 |
| JP | 02-188527 | 7/1990 |
| JP | 03-017076 | 2/1991 |
| JP | 60-072868 | 3/1994 |
| JP | 10-059948 | 3/1998 |
| JP | 11-506723 | 6/1999 |
| JP | 2000-020681 | 1/2000 |
| JP | 2001-501965 | 2/2001 |
| JP | 2001-201454 | 7/2001 |
| JP | 2001-519754 | 10/2001 |
| JP | 2005-503423 | 2/2005 |
| JP | 2005-097120 | 4/2005 |
| JP | 2007-530529 | 11/2007 |
| JP | 2008-545777 | 12/2008 |
| JP | 4521187 | 8/2010 |
| WO | WO 86/04991 | 8/1986 |
| WO | WO 93/12496 | 6/1993 |
| WO | WO 96/40687 | 12/1996 |
| WO | WO 97/02819 | 1/1997 |
| WO | WO 97/44063 | 11/1997 |
| WO | WO 98/17678 | 4/1998 |
| WO | WO 98/52898 | 11/1998 |
| WO | WO 99/26661 | 6/1999 |
| WO | WO 01/91011 | 11/2001 |
| WO | WO 02/28881 | 4/2002 |
| WO | WO 02/43652 | 6/2002 |
| WO | WO 03/026563 | 4/2003 |
| WO | WO 03/061656 | 7/2003 |
| WO | WO 03/062942 | 7/2003 |
| WO | WO 2005/032474 | 4/2005 |
| WO | WO 2005/092392 | 10/2005 |
| WO | WO 2006/027711 | 3/2006 |
| WO | WO 2006/058219 | 6/2006 |
| WO | WO 2006/131923 | 12/2006 |
| WO | WO 2007/050318 | 5/2007 |
| WO | WO 2007/139818 | 12/2007 |
| WO | WO 2008/010222 | 1/2008 |
| WO | WO 2008/010223 | 1/2008 |
| WO | WO 2009/101616 | 8/2009 |
| WO | WO 2011/104637 | 9/2011 |
| WO | WO 2012/038963 | 3/2012 |

OTHER PUBLICATIONS

Geffen et al., European Neuropsychopharmacology., Mar. 19, 2008, 19, 1-13.*
Schultz et al., American Family Physician, Jun. 15, 2007, 75, 1821-1829.*
Drugs.com, BioLineRx Successfully Completes Phase 1 Clinical Trials of BL-1020, Feb. 13, 2007.*
The Negative Symptoms of Schizophrenia (The Harvard Medical School Family Health Guide, President & Fellows of Harvard College 2006).*
Response Dated Nov. 24, 2011 to Official Action of Aug. 25, 2011 From the U.S. Appl. No. 12/655,048.
Supplemental After Final Amendment Dated Nov. 17, 2011 in Response to Official Action Dated Aug. 5, 2011 From the U.S. Appl. No. 12/764,124.
Translation of Office Action Dated Nov. 3, 2011 From the State Intellectual Property Office of the People's Republic of China Re.: Application No. 200580017025.1.
International Search Report and the Written Opinion Dated Dec. 1, 2011 From the International Searching Authority Re. Application No. PCT/IB2011/000915.
Notice of Allowance Dated Dec. 1, 2011 From the U.S. Appl. No. 12/764,124.
Official Action Dated Nov. 22, 2011 From the U.S. Appl. No. 12/309,361.
Benja-Athon.
Communication Pursuant to Article 94(3) EPC Dated Jan. 26, 2012 From the European Patent Office Re. Application No. 10182948.9.
Examination Report Dated Jan. 19, 2012 From the Instituto Mexicano de la Propriedad Industrial Re. Application No. MX/a/2007/015511 and Its Translation Into English.
International Search Report and the Written Opinion Dated Feb. 8, 2012 From the International Searching Authority Re.: Application No. PCT/IL2011/000752.
Official Action Dated Feb. 2, 2012 From the U.S. Appl. No. 12/655,048.
Summons to Attend Oral Proceedings Pursuant to Rule 115(1) EPC Dated Jan. 26, 2012 From the European Patent Office Re. Application No. 06756205.8.
Rephaeli et al. "Gamin-Aminobutyric Acid Amides of Nortriptyline and Fluoxetine Display Improved Pain Suppressing Activity", Journal of Medicinal Chemistry, XP002668033, 52(9): 3010-3017, 2009. Scheme 1, Experimental Section.
Communication Under Rule 71(3) EPC Dated Feb. 20, 2012 From the European Patent Office Re. Application No. 09711260.1.
Notice of Allowance Dated Feb. 23, 2012 From the U.S. Appl. No. 12/867,055.
Translation of Office Action Dated Feb. 23, 2012 From the State Intellectual Property Office of the People's Republic of China Re. Application No. 200780033294.6.
Translation of Office Action Dated Jan. 30, 2012 From the State Intellectual Property Office of the People's Republic of China Re.: Application No. 200680029378.8.
Examination Report Dated Jun. 16, 2011 From the Instituto Mexicano de la Propriedad Industrial Re. Application No. PA/a/2006/010924.
Translation of Notice of Final Rejection Dated May 30, 2011 From the Korean Intellectual Property Office Re. Application No. 2010-7016372.
Translation of Notice of Final Rejection Dated May 30, 2011 From the Korean Intellectual Property Office Re.: Application No. 2009-7024590.
Communication Under Rule 71(3) EPC Dated May 7, 2012 From the European Patent Office Re.: Application No. 06756205.8.
Requisition by the Examiner Dated Apr. 13, 2012 From the Canadian Intellectual Property Office Re. Application No. 2,461,663.
Translation of Decision on Rejection Dated May 30, 2012 From the State Intellectual Property Office of the People's Republic of China Re.: Application No. 200580017025.1.
Examination Report Dated Jun. 8, 2011 From the Instituto Mexicano de la Propriedad Industrial Re. Application No. MX/a/2007/015511 and Its Summary Into English.
Response Dated Feb. 25, 2011 to Official Action of Aug. 25, 2010 From the U.S. Appl. No. 12/764,124.
Office Action Dated Mar. 2, 2011 From the Israeli Patent Office Re. Application No. 196538.
Response Dated Aug. 2, 2011 to Office Action of Mar. 2, 2011 From the Israeli Patent Office Re. Application No. 196538.
Response Dated Jul. 24, 2011 to Communication Pursuant to Article 94(3) EPC of Apr. 11, 2011 From the European Patent Office Re. Application No. 09711260.1.
Response Dated Jul. 26, 2011 to Official Action of Mar. 14, 2011 From the U.S. Appl. No. 12/764,124.
Response Dated Jul. 26 To Communication Pursuant to Rules 70(2) and 70a(2) EPC of Jan. 31, 2011 From the European Patent Office Re. Application No. 10182948.9.
Official Action Dated Oct. 21, 2011 From the U.S. Appl. No. 12/373,542.
Response Dated Oct. 19, 2011 to Official Action Dated Aug. 5, 2011 From the U.S. Appl. No. 12/764,124.
Response Dated Oct. 23, 2011 to Office Action Dated May 17, 2011 From the Israel Patent Office Re.: Application No. 187892.
Bousquet et al. "Synthesis, Physical Properties, Toxicological Studies and Bioavailability of L-Pyroglutamic and L-Glutamic Acid Esters of Paracetamol as Potentially Prodrugs", Journal of Pharmacy and Pharmacology, 48: 479-485, Jan. 1996.

(56) References Cited

OTHER PUBLICATIONS

Requisition Dated Aug. 2, 2011 From the Canadian Intellectual Property Office Re. Application No. 2,461,663.
Communication Under Rule 71(3) EPC Dated Nov. 28, 2011 From the European Patent Office Re. Application No. 07789958.1.
Translation of Notice of Reason for Rejection Dated Nov. 29, 2011 From the Japanese Patent Office Re. Application No. 2008-515378.
Office Action Dated Dec. 12, 2011 From the Israel Patent Office Re.: Application No. 187892 and Its Translation Into English.
Applicant-Initiated Interview Summary Dated Apr. 19, 2012 From the U.S. Appl. No. 12/655,048.
Notice of Allowance Dated Apr. 12, 2012 From the U.S. Appl. No. 12/373,542.
Official Action Dated May 3 From the U.S. Appl. No. 11/921,578.
Official Action Dated Mar. 14, 2011 From the U.S. Appl. No. 12/764,124.
Response Dated Jul. 6, 2011 to Official Action of Mar. 14, 2011 From the U.S. Appl. No. 12/764,124.
Official Action Dated Jun. 23, 2011 From the U.S. Appl. No. 12/373,542.
Official Action Dated Aug. 5, 2011 From the U.S. Appl. No. 12/764,124.
Response Dated Aug. 22, 2011 to Office Action of Jun. 24, 2011 From the State Intellectual Property Office of the People's Republic of China Re. Application No. 200780033294.6.
Official Action Dated Aug. 25, 2011 From the U.S. Appl. No. 12/655,048.
Requisition Dated Aug. 2, 2011 From the Canadian Intellectual Property Office Re. Application No. 2,560,905.
Response Dated Sep. 18, 2011 to Examination Report of Jun. 16, 2011 From the Instituto Mexicano de la Propriedad Industrial Re. Application No. PA/a/2006/010924.
Advisory Action Before the Filing of an Appeal Brief Dated Oct. 25, 2011 From the U.S. Appl. No. 12/764,124.
Examiner's Report Dated Oct. 7, 2011 From the Australian Government, IP Australia Re. Application No. 2007274583.
Translation of Notice of Reason for Rejection Dated Sep. 30, 2011 From the Japanese Patent Office Re. Application No. 2007-504560.
Advisory Action Before the Filing of an Appeal Brief Dated Jan. 10, 2012 From the U.S. Appl. No. 12/655,048.
Examination Report Dated Dec. 5, 2011 From the Instituto Mexicano de la Propriedad Industrial Re. Application No. MX/a/2009/000641 and Its Summary in English.
Examiner's Report Dated Jan. 24, 2012 From the Australian Government, IP Australia Re. Application No. 2006256369.
Translation of Office Action Dated Jan. 5, 2012 From the State Intellectual Property Office of the People's Republic of China Re. Application No. 200810190781.X.
International Preliminary Report on Patentability Dated Oct. 17, 2007 From the International Preliminary Examining Authority Re.: Application No. PCT/IL2006/000666.
"New Edition of Pharmaceutics", People's Hygiene Publishing House, 14: 178, 1998. Abstract in Chinese Only!
Communication Pursuant to Article 94(3) Dated Apr. 2, 2008 From the European Patent Office Re.: Application No. 06756205.8.
Communication Pursuant to Article 94(3) EPC Dated Apr. 11, 2011 From the European Patent Office Re. Application No. 09711260.1.
Communication Pursuant to Article 94(3) EPC Dated Dec. 16, 2010 From the European Patent Office Re. Application No. 02772790.8.
Communication Pursuant to Article 94(3) EPC Dated Nov. 24, 2010 From the European Patent Office Re. Application No. 07789958.1.
Communication Pursuant to Article 96(2) EPC Dated Nov. 24, 2006 From the European Patent Office Re.: Application No. 02772790.8.
Communication Pursuant to Rules 70(2) and 70a(2) EPC Dated Jan. 31, 2011 From the European Patent Office Re. Application No. 10182948.9.
Communication Relating to the Results of the Partial International Search Dated May 10, 2007 From the International Searching Authority Re.: Application No. PCT/IL2006/000666.
Communication Relating to the Results of the Partial International Search Dated Jun. 13, 2006 From the International Searching Authority Re.: Application No. PCT/IL2005/000341.
Communication Relating to the Results of the Partial International Search Dated Nov. 20, 2007 From the International Searching Authority Re.: Application No. PCT/IL2007/000902.
Communication Relating to the Results of the Partial International Search Dated Nov. 27, 2007 From the International Searching Authority Re.: Application No. PCT/IL2007/000903.
Communication Under Rule 112 EPC Dated Oct. 2, 2007 From the European Patent Office Re.: Application No. 05718914.4.
European Search Report and the European Search Opinion Dated Dec. 30, 2010 From the European Patent Office Re. Application No. 10182948.9.
Examination Report Dated Aug. 25, 2010 From the Instituto Mexican de la Propriedad Industrial Re. Application No. PA/a/2004/002912 and Its Summary in English.
Examiner's Report Dated May 23, 2007 From the Government of India Patent Office Re.: Application No. 642/CHENP/2004-SPS.
Examiner's Report Dated May 2, 2007 From the Australian Government, IP Australia Re.: Application No. 2004201240.
Examiner's Report Dated Oct. 21, 2010 From the Australian Government, IP Australia Re. Application No. 2006256369.
Examiner's Report Dated Feb. 24, 2010 From the Australian Government, IP Australia Re.: Application No. 2008243147.
International Preliminary Report on Patentability Dated Dec. 3, 2007 From the International Preliminary Examining Authority Re.: Application No. PCT/IL2006/000666.
International Preliminary Report on Patentability Dated Oct. 12, 2006 From the International Bureau of WIPO Re.: Application No. PCT/IL2005/000341.
International Preliminary Report on Patentability Dated Aug. 26, 2010 From the International Bureau of WIPO Re. Re. Application No. PCT/IL2009/000158.
International Preliminary Report on Patentability Dated Jan. 29, 2009 From the International Bureau of WIPO Re.: Application No. PCT/IL2007/000902.
International Preliminary Report on Patentability Dated Jan. 29, 2009 From the International Bureau of WIPO Re.: Application No. PCT/IL2007/000903.
International Search Report and the Written Opinion Dated Dec. 3, 2007 From the International Searching Authority Re.: Application No. PCT/IL2006/000666.
International Search Report and the Written Opinion Dated Feb. 12, 2008 From the International Searching Authority Re.: Application No. PCT/IL2007/000903.
International Search Report and the Written Opinion Dated Feb. 13, 2008 From the International Searching Authority Re.: Application No. PCT/IL2007/000902.
International Search Report and the Written Opinion Dated Aug. 23, 2006 From the International Searching Authority Re.: Application No. PCT/IL2005/000341.
International Search Report and the Written Opinion Dated Jun. 25, 2009 From the International Searching Authority Re. Application No. PCT/IL2009/000158.
International Search Report and the Written Opinion Dated Mar. 30, 2011 From the International Searching Authority Re. Application No. PCT/IL2010/01041.
International Search Report Dated Jul. 11, 2003 From the International Searching Authority Re.: Application No. PCT/IL02/00795.
Interview Summary Dated May 6, 2011 From the U.S. Appl. No. 12/656,048.
Invitation to Pay Additional Fees Dated Jun. 13, 2006 From the International Searching Authority Re.: Application No. PCT/IL2005/000341.
Invitation to Pay Additional Fees Dated Nov. 20, 2007 From the International Searching Authority Re.: Application No. PCT/IL2007/000902.
Invitation to Pay Additional Fees Dated Nov. 27, 2007 From the International Searching Authority Re.: Application No. PCT/IL2007/000903.
Notice of Allowance Dated Jul. 10, 2009 From the U.S. Appl. No. 11/636,599.

(56) References Cited

OTHER PUBLICATIONS

Notice of Allowance Dated Mar. 11, 2008 From the U.S. Appl. No. 10/808,541.
Notice of the Reason for Rejection Dated Mar. 26, 2010 From the Korean Intellectual Property Office Re.: Application No. 2004-7004581. Korean Only.
Office Action Dated Mar. 2, 2011 From the Israel Patent Office Re. Application No. 196538 and Its Translation Into English.
Office Action Dated Jun. 6, 2010 From the Israeli Patent Office Re.: Application No. 161083 and Its Translation Into English.
Office Action Dated Aug. 8, 2008 From the Patent Office of the People's Republic of China Re.: Application No. 02823600.9.
Office Action Dated Sep. 9, 2005 From the Patent Office of the People's Republic of China Re.: Application No. 02823600.9 and Its Translation Into English.
Office Action Dated Feb. 14, 2008 From the Government of India Patent Office Re.: Application No. 642/CHENP/2004-SPS.
Office Action Dated Feb. 15, 2009 From the Israeli Patent Office Re.: Application No. 161083.
Office Action Dated May 15, 2008 From the Government of India Patent Office Re.: Application No. 642/CHENP/2004-SPS.
Office Action Dated Aug. 23, 2010 From the Israel Patent Office Re. Application No. 203058 and Its Translation Into English.
Office Action Dated Apr. 25, 2010 From the Israel Patent Office Re.: Application No. 187892 and Its Translation Into English.
Office Action Dated Feb. 27, 2009 From the Israeli Patent Office Re.: Application No. 161083 and Its Translation Into English.
Office Action Dated Jul. 27, 2010 From the Israel Patent Office Re.: Application No. 199877 and Its Translation Into English.
Official Action Dated Feb. 1, 2007 From the U.S. Appl. No. 10/808,541.
Official Action Dated Jan. 6, 2011 From the U.S. Appl. No. 12/656,048.
Official Action Dated May 9, 2008 From the U.S. Appl. No. 11/636,599.
Official Action Dated Dec. 14, 2010 From the U.S. Appl. No. 12/585,021.
Official Action Dated Feb. 16, 2010 From the U.S. Appl. No. 12/585,021.
Official Action Dated May 16, 2008 From the U.S. Appl. No. 11/636,594.
Official Action Dated Sep. 16, 2008 From the U.S. Appl. No. 12/005,342.
Official Action Dated Apr. 17, 2008 From the U.S. Appl. No. 11/636,594.
Official Action Dated Feb. 17, 2009 From the U.S. Appl. No. 11/636,599.
Official Action Dated Jun. 17, 2010 From the U.S. Appl. No. 12/585,021.
Official Action Dated Jun. 19, 2008 From the U.S. Appl. No. 11/636,599.
Official Action Dated Aug. 25, 2010 From the U.S. Appl. No. 12/764,124.
Official Action Dated Jul. 25, 2006 From the U.S. Appl. No. 10/808,541.
Official Action Dated Mar. 30, 2006 From the U.S. Appl. No. 10/808,541.
Official Action Dated Oct. 31, 2008 From the U.S. Appl. No. 12/005,342.
Requisition Dated Nov. 8, 2010 From the Canadian Intellectual Property Office Re. Application No. 2,461,663.
Response Dated Sep. 1, 2010 to Office Action of Apr. 25, 2010 From the Israel Patent Office Re.: Application No. 187892.
Response Dated Mar. 3, 2010 to Official Action of Feb. 16, 2010 From the U.S. Appl. No. 12/585,021.
Response Dated Oct. 5, 2010 to Official Action of Jun. 17, 2010 From the U.S. Appl. No. 12/585,021.
Response Dated Jun. 6, 2010 to Office Action of Jan. 29, 2010 From the State Intellectual Property Office of the People's Republic of China Re.: Application No. 200680029378.8.
Response Dated Nov. 8, 2010 to Office Action of Jul. 12, 2010 From the State Intellectual Property Office of the People's Republic of China Re. Application No. 200780033294.6.
Response Dated Feb. 9, 2011 to Office Action of Aug. 11, 2010 From the State Intellectual Property Office of the People's Republic of China Re. Application No. 200810190781.X.
Response Dated Jan. 13, 2010 to Notice for Reason for Rejection of Oct. 20, 2009 From the Japanese Patent Office Re.: Application No. 2003-530202.
Response Dated Jan. 13, 2010 to Office Action of Jul. 17, 2009 From the State Intellectual Property Office of the People's Republic of China Re.: Application No. 200580017025.1.
Response Dated Nov. 16, 2010 to Examination Report of Aug. 25, 2010 From the Instituto Mexicano de la Propriedad Industrial Re. Application No. PA/a/2004/002912.
Response Dated Jan. 18, 2011 to Notice of Reason for Rejection of Nov. 2, 2010 From the Japanese Patent Office Re. Application No. 2007-504560.
Response Dated Dec. 20, 2010 to Notice of the Reason for Rejection of Oct. 28, 2010 From the Korean Itellectual property Office Re. Application No. 2010-7016372.
Response Dated Mar. 22, 2011 to Final Notice of the Reason for Rejection of Nov. 24, 2010 From the Korean Intellectual Property Office Re.: Application No. 2009-7024590.
Response Dated Dec. 23, 2010 to Office Action of Aug. 23, 2010 From the Israel Patent Office Re. Application No. 203058.
Response Dated Feb. 23, 2011 to Examiner's Report of Feb. 24, 2010 From the Australian Government, IP Australia Re.: Application No. 2008243147.
Response Dated Jun. 23, 2010 to Notice of the Reason for Rejection of Feb. 24, 2010 From the Korean Intellectual Property Office Re.: Application No. 2009-7024590.
Response Dated Jun. 23, 2010 to Notice of the Reason for Rejection of Mar. 26, 2010 From the Korean Intellectual Property Office Re.: Application No. 2004-7004581.
Response Dated Nov. 23, 2009 to Office Action of Jul. 23, 2009 From the Israel Patent Office Re.: Application No. 199877.
Response Dated Mar. 24, 2011 to Communication Pursuant to Article 94(3) EPC of Nov. 24, 2010 From the European Patent Office Re. Application No. 07789958.1.
Response Dated Nov. 28, 2010 to Office Action of Jul. 27, 2010 From the Israel Patent Office Re.: Application No. 199877.
Response Dated Dec. 30, 2009 to Office Action of Aug. 31, 2009 From the Israel Patent Office Re.: Application No. 161083.
Supplementary European Search Report Dated Apr. 25, 2006 From the European Patent Office Re.: Application No. 02772790.8.
Translation of Final Notice of the Reason for Rejection Dated Nov. 24, 2010 From the Korean Intellectual Property Office Re.: Application No. 2009-7024590.
Translation of Notice for Reason for Rejection Dated Oct. 20, 2009 From the Japanese Patent Office Re.: Application No. 2003-530202.
Translation of Notice of Reason for Rejection Dated Nov. 2, 2010 From the Japanese Patent Office Re. Application No. 2007-504560.
Translation of Notice of Reason for Rejection Dated Feb. 10, 2009 From the Japanese Patent Office Re.: Application No. 2003-530202.
Translation of Notice of the Reason for Rejection Dated Feb. 24, 2010 From the Korean Intellectual Property Office Re.: Application No. 2009-7024590.
Translation of Notice of the Reason for Rejection Dated Aug. 26, 2009 From the Korean Intellectual Property Office Re.: Application No. 2004-7004581.
Translation of Notice of the Reason for Rejection Dated Mar. 26, 2010 From the Korean Intellectual Property Office Re.: Application No. 2004-7004581.
Translation of Notice of the Reason for Rejection Dated Oct. 28, 2010 From the Korean Itellectual property Office Re. Application No. 2010-7016372.
Translation of Office Action Dated Aug. 11, 2010 From the State Intellectual Property Office of the People's Republic of China Re. Application No. 200810190781.X.
Translation of Office Action Dated Jul. 12, 2010 From the State Intellectual Property Office of the People's Republic of China Re. Application No. 200780033294.6.

(56) References Cited

OTHER PUBLICATIONS

Translation of Office Action Dated Jul. 17, 2009 From the State Intellectual Property Office of the People's Republic of China Re.: Application No. 200580017025.1.
Translation of Office Action Dated Jan. 29, 2010 From the State Intellectual Property Office of the People's Republic of China Re.: Application No. 200680029378.8.
Written Opinion Dated Feb. 13, 2008 From the International Searching Authority Re.: Application No. PCT/IL2007/000902.
Written Opinion Dated Aug. 23, 2006 From the International Searching Authority Re.: Application No. PCT/IL2005/000341.
Written Opinion Dated Jun. 25, 2009 From the International Searching Authority Re. Application No. PCT/IL2009/000158.
BioLineRx "BioLineRx Announces Positive Topline Results for BL-1020, A First in Class GABA Enhanced Antipsychotic for the Treatment of Schizophrenia. BL-1020 Meets Primary and Secondary Efficacy Endpoints From the Pahasc 2b EAGLE Trial", BioLine Rx, 4 P., Sep. 14, 2009.
Budavari et al. "The Merck Index", Merck & Co., USA, 12th Ed., 1996. P.THER-8, First col., 6th Line From the Bottom, 2nd col., Line 13.
Budavari et al. "The Merck Index", Merck & Co., USA, 12th Ed, 1996, p. 1260. p. 1260, § 1.
Budavari et al. "The Merck Index", Merck & Co., USA, 12th Ed., 1996, p. 1246. p. 1246, Last §.
Capasso et al. "Anticonvulsive Activity of a New GABA Mimetic Drug", European Neuropsychopharmacology, 7: 57-63, 1997.
Carducci et al. "Phenylbutyrate Induces Apoptosis in Human Prostate Cancer and Is More Potent Than Phenylacetate", Clinical Cancer Research, XP002613699, 2(2): 379-387, 1996. Abstract.
Chan et al. "Phenothiazine Inhibitors of Trypanothione Reductase as Potential Antitrypanosomal and Antileishmanial Drugs", Journal of medicinal Chmeistry, 41(2): 148-156, 1998.
Coradini et al. "Effect of Sodium Butyrate on Human Breast Cancer Cell Lines", Cell Proliferation, XP002613698, 30(3-4) Mar. 1997. Abstract.
Degrand et al. "Synthesis of Nitroxides for Use as Procationic Labels and Their Incorporation Into Nafion Films", The Journal of Organic Chemistry, 58(9): 2573-2577, 1993.
Dutta et al. "Existing Dopaminergic Therapies for Parkinson's Disease", Expert Opinion on Therapeutic Patents, XP002531574, 16: 1613-1625, 2006. § [04.1], Fig.1.
Fingl et al. "General Principles", The Pharmacological Basis of Therapeutics, Chap.1: 1-46, 1975.
Florence et al. "Prolongation of the Action of Intramuscular Formulations of Phenothiazines", Optimization of Drug Delivery, 17th Alfred Benzon Symposium, Mungsgaard, Copenhagen, p. 93-111, 1982.
Geyer et al. "Animal Behavior Models of the Mechanisms Underlying Antipsychotic Atypicality", Progress in Neuro-Psychopharmacology & Biological Psychiatry, 27: 1071-1079, 2003.
Gil-Ad et al. "Novel Anti-Psychotics That Display GABAergic Acitivity and Decreased Extrapyramidal Side Effects, for the Treatment of Schizophrenia and Related Psychiatric Disorders", Neural Plasticity, 10(3): 200, 2003. Abstract.
Hadad et al. "Pharmacokinetic Analysis and Antiepileptic Activity of N-Valproyl Derivatives of GABA and Glycine", Pharmaceutical Research, XP008038069, 112(6): 905-910, Jan. 1, 1995. Abstract, p. 906, Compound IV, p. 909, r-h col., § 1.
K?pf-Maier et al. "An Organoid Culture Assay (OCA) for Determining the Drug Sensitivity of human Tumors", Int. J. Cancer, 51: 99-107, 1992.
Lloyd et al. "The Potential Use of GABA Agonists in Psychiatric Disorders: Evidence From Studies With Progabide in Animal Models and Clinical Trials", Pharmacology, Biochemistry & Behavior, 18: 957-966, 1983.
Luo "Pharmacokinetic Studies of Fluphenazine and Four Ester Prodrugs", A Thesis Submitted to the College of Graduate Studies and Research in Partial Fulfillment of the Requirements for the Degree of Doctor of Philosophy in the College of Pharmacy and Nutrition, University Saskatchewan, Saskatoon, Saskatchewan, Canada, p. 1-171, 1999. p. 5, § 1.2.1.1, p. 19, Compounds, p. 39, § 3.2.2.0, p. 147-152.
Luo et al. "Comparative Pharmacokinetic Analysis of Fluphenazine and Four Ester Prodrugs", Pharmaceutical Research, XP008130430, 14(11 Suppl.): S360, # 2441, Nov. 1997. & Annual Meeting of the American Association of Pharmaceutical Scientists, Boston, MA, USA, Nov. 2-6, 1997.
McCaffrey et al. "A Rapid Fluorometric DNA Assay for the Measurement of Cell Density and Proliferation In Vitro", In Vitro Cellular Development Biology, 24(3): 247-252, 1988. Abstract.
Merck "Schizophrenia", the Merck Manuals, Section Psychiatric Disorders, 17th Ed.: 1569-1575, Dec. 10, 1999. Japanese Version and Its Translation Into English. p. 1572, Right col., Line 15—p. 1573, Left col., Line 11, p. 1574, Table 193-1.
Milovic "Effect of Structural Analogues of Propionate and Butyrate on Colon Cancer Cell Growth", International Journal of Colorectal Disease, XP002613700, 15(5-6): 264-270, 2000. Abstract, p. 267, Table 2.
Napolitano et al. "New Directions in Parkinson's Research and Treatment", Expert Opinion on Therapeutic Patents, XP002531575, 8: 1251-1268, 1998. Fig.4.
Nicoletti et al. "A Rapid and Simple Method for Measuring Thymocyte Apoptosis by Propidium Iodide Staining and Flow Cytometry", Journal of Immunological Methods, 139: 271-279, 1991.
Nordenberg et al. "Effects of Psychotropic Drugs on Cell Proliferation and Differentiation", Biochemical Pharmacology, XP001027786, 58(8): 1229-1236, Oct. 15, 1999. Abstract, p. 1231, r-h col., § 2—p. 1232, 1-h col., § 2.
Octonus "Octonus: Diamond Calculator", Dec. 2000.
Ogiso et al. "Pharmacokinetic Analysis of Phenytoin and Its Derivatives in Plasma and Brain in Rats", Biological and Pharmaceutical Bulletin, XP002613683, 16(10): 1025-1030, Oct. 1, 1993. Fig.1, Compound 3, p. 1025, 1-h col., § 1, r-h col., § 1.
Pouzet et al. "Effects of the 5-HT7 Receptor Antagonist SB-258741 in Animal Models for Schizophrenia", Pharmacology, Biochemistry and Behavior, 71: 655-665, 2002.
Prasad "Butyric Acid: A Small Fatty Acid With Diverse Biological Functions", Life Science, 27(15): 1351-1358, 1980.
Quadri et al. "Effects of Centrally Acting Drugs on Serum Prolactin Levels in Rhesus Monkeys", Neuroendocrinology, 27(3-4): 136-147, 1978. Abstract.
Rephaeli et al. "Observation of Sequence-Dependent Interaction Between Prodrugs of Carboxylic-Acid-Esters and Doxorubicin in Cancer Cells", Proceedings of the American Association for Cancer Research, Annual Meeting, 40: 592-, 1999. Abstract. & 90th Annual Meeting of the American Association for Cancer Research, Philadelphia, PA, USA, 1999.
Sakamoto et al. "Studies on Prodrugs. VI. Preparation and Characterization of 95-Substituted 2-Oxo-1,3-Dioxol-4-yl)Methyl Esters of Mecillinam", Chemical and Pharmaceutical Bulletin, 35(2): 642-646, 1987. Abstract.
Scriba "Phenytoin-Lipid Conjugates as Potential Prodrugs of Phenytoin", Archiv der Pharmazie, VCII—Verlagsgesellschaft MBII, Weinheim, DE, 326(8): 477-481, 1993. Scheme 1, p. 147.
Scriba et al. "Anticonvulsant Activity of Phenytoin-Lipid Conjugates, A New Class of Phenytoin Prodrugs"—Journal of Pharmaceutical Pharmacology, 47: 197-203, 1996. Scheme 1, p. 198, Abstract.
Scriba et al. "Synthesis and Anticovulsant Activity of N-Benzyloxycarbonyl-Amino Acid Prodrugs of Phenytoin", Journal of Pharmacy and Pharmacology, XP008069882, 51(5): 549-553, May 1, 1999. Abstract, Fig. 1.
Shalitin et al. "The Effect of Angiotensin II on Myosin Heavy Chain Expression in Cultured Myocardial Cells", In Vitro Cellular Development Biology—Animal, 32: 573-578, 1996.
Toth "A Novel Chemical Approach to Drug Delivery: Lipidic Amino Acid Conjugates", Journal of Drug Targeting, 2(3): 217-239, 1994. p. 223, col. II, 3rd §.
Velázquez et al. "Butyrate Inhibits Seeding and Growth of Colorectal Metastases to the Liver in Mice", Surgery, XP005473855, 120(2): 440-448, Aug. 1, 1996. Abstract.

(56) References Cited

OTHER PUBLICATIONS

Vezin et al. "Biological Active Poly(N-Metacryloy1-?-Amino Acid) Esters of Fluphenazine and Their Duration of Activity", Journal of Pharmacy and Pharmacology, British Pharmacology Conference 1979, 31(Suppl.): 63P, 1979.
Ware et al. "An Automated Approach to Salt Selection for New Unique Trazodone Salts", Pharmaceutical Research, 21(1): 177-184, 2004. Abstract.
Wilson et al. "Central Nervous System Depressant", Wilson and Gisvold's Textbook of Organic Medicinal and Pharmaceutical Chemistry, 8th Ed., p. 362-371, 1982.
Wolffe "Transcriptional Control. Sinful Repression", Nature, 387: 16017, 1997.
Worms et al. "Dopamine-Like Activities of an Aminopyridazinde Derivative, CM 30366: A Behavioural Study", Naunyn-Schmiedeberg's Archives of Pharmacology, 334: 246-252, 1986.
Yogev-Falach et al. "The Importance of Propargylamine Moiety in the Anti-Parkinson Drug Rasagiline and Its Derivatives in MAPK-Dependent Amyloid Precursor Protein Processing", The FASEB Journal, 17: 2325-2327, 2003. Abstract.
Zaugg et al. "Modification of Hemoglobin With Analogs of Aspirin", The Journal of Biological Chemistry, 255(7): 2816-2821, 1980.
Examination Report Dated May 30, 2011 From the Instituto Mexicano de la Propriedad Industrial Re. Application No. PA/a/2004/002912 and Its Summary in English.
Notice of Allowance Dated May 29, 2009 From the U.S. Appl. No. 12/005,342.
Office Action Dated May 17, 2011 From the Israel Patent Office Re.: Application No. 187892 and Its Translation Into English.
Response Dated May 1, 2006 to Official Action of Mar. 30, 2006 From the U.S. Appl. No. 10/808,541.
Response Dated Dec. 3, 2007 to Official Action of Feb. 1, 2007 From the U.S. Appl. No. 10/808,541.
Response Dated Oct. 13, 2008 to Official Action of Sep. 16, 2008 From the U.S. Appl. No. 12/005,342.
Response Dated Nov. 15, 2006 to Official Action of Jul. 25, 2006 From the U.S. Appl. No. 10/808,541.
Response Dated Feb. 24, 2009 to Official Action of Oct. 31, 2008 From the U.S. Appl. No. 12/005,342.
Supplemental Response Dated Mar. 31, 2009 to Response of Feb. 24, 2009 From the U.S. Appl. No. 12/005,342.
Response Dated Sep. 7, 2011 to Official Action of Jul. 12, 2011 From the U.S. Appl. No. 11/921,578.
Translation of Final Notice of the Reason for Rejection Dated Aug. 31, 2011 From the Korean Intellectual Property Office Re. Application No. 2010-7016372.
Communication Under Rule 71(3) EPC Dated Sep. 21, 2011 From the European Patent Office Re. Application No. 02772790.8.
Response Dated Oct. 3, 2011 to Office Action of Jun. 6, 2010 From the Israeli Patent Office Re.: Application No. 161083.
Response Dated Dec. 14, 2011 to Notice of Reason for Rejection of Sep. 30, 2011 From the Japanese Patent Office Re. Application No. 2007-504560.
Response Dated Dec. 15, 2011 to Examiner's Report of Oct. 21, 2010 From the Australian Government, IP Australia Re. Application No. 2006256369.
Response Dated Aug. 23, 2011 to Official Action of Jun. 23, 2011 From the U.S. Appl. No. 12/373,542.
Response Dated Jul. 20, 2011 to Notice of Final Rejection of May 30, 2011 From the Korean Intellectual Property Office Re. Application No. 2010-7016372.
Restriction Official Action Dated Dec. 20, 2011 From the U.S. Appl. No. 13/034,453.
Official Action Dated Jan. 31, 2012 From the U.S. Appl. No. 12/309,361.
Official Action Dated Jan. 31, 2012 From the U.S. Appl. No. 13/034,453.
Morissette et al. "High-Througput Crystallization: Polymorphs, Salts, Co-Crystals and Solvates of Pharmaceutical Solids", Advanced Drug Delivery Reviews, 56: 275-300, 2004.
International Preliminary Report on Patentability Dated Jun. 21, 2012 From the International Bureau of WIPO Re. Application No. PCT/IL2010/01041.
Translation of Notice of the Reason for Rejection Dated Jun. 1, 2012 From the Korean Patent Office Re. Application No. 2012-7002565.
English Summary of Examination Report Dated Sep. 4, 2007 From the Instituto Mexicano de la Propriedad Industrial Re. Application No. PA/a/2004/002912.
Examination Report Dated Sep. 20, 2010 From the Instituto Mexicano der la Propriedad Industrial Re. Application No. MX/a/2007/015511 and Its Translation Into English.
Office Action Dated Jun. 24, 2011 From the State Intellectual Property Office of the People's Republic of China Re. Application No. 200780033294.6 and Its Translation Into English.
Response Dated May 5, 2011 to Requisition of Nov. 8, 2010 From the Canadian Intellectual Property Office Re. Application No. 2,461,663.
Response Dated Jun. 6, 2011 to Official Action of Jan. 6, 2011 From the U.S. Appl. No. 12/656,048.
Response Dated Feb. 18, 2011 to Examination Report Dated Sep. 20, 2010 From the Instituto Mexicano der la Propriedad Industrial Re. Application No. MX/a/2007/015511 and Its Translation Into English.
Official Action Dated Nov. 1, 2011 From the U.S. Appl. No. 11/921,578.
Bastin et al. "Salt Selection and Optimisation Procedures for Pharmaceutical New Chemical Entities", Organic Process Research & Development, 4: 427-435, 2000.
Interview Summary Dated Jan. 27, 2011 From the U.S. Appl. No. 12/585,021.
Notice of Allowance Dated Mar. 21, 2011 From the U.S. Appl. No. 12/585,021.
Official Action Dated Jul. 12, 2011 From the U.S. Appl. No. 11/921,578.
Response Dated Mar. 9, 2011 to Official Action of Dec. 14, 2010 From the U.S. Appl. No. 12/585,021.
Response Dated Jun. 16, 2011 to Communication Pursuant to Article 94(3) EPC of Dec. 16, 2010 From the European Patent Office Re. Application No. 02772790.8.
Response Dated Oct. 3, 2011 to Examination Report of Jun. 8, 2011 From the Instituto Mexicano de la Propriedad Industrial Re. Application No. MX/a/2007/015511.
Translation of Office Action Dated Apr. 25, 2013 From the State Intellectual Property Office of the People's Republic of China Re. Application No. 201080062943.7.
Translation of Search Report Dated Apr. 25, 2013 From the State Intellectual Property Office of the People's Republic of China Re. Application No. 201080062943.7.
Restriction Official Action Dated Aug. 5, 2013 From the U.S. Appl. No. 13/825,369.
Haynes et al. "Occurrence of Pharmaceutically Acceptable Anions and Cations in the Cambridge Structural Database", Journal of Pharmaceutical Sciences, 94(10): 2111-2120, Oct. 2005.
Notice of Reason for Rejection Dated Oct. 24, 2014 From the Japanese Patent Office Re. Application No. 2012-542686 and its Machine Translation Into English.

\* cited by examiner

METHODS OF IMPROVING COGNITIVE FUNCTIONS

This application claims the benefit of priority to U.S. Provisional Application No. 61/267,883, filed Dec. 9, 2009 and entitled "METHODS OF IMPROVING COGNITIVE FUNCTIONS"; the contents of which are hereby incorporated by reference herein in its entirety for all purposes.

FIELD AND BACKGROUND OF THE INVENTION

The present invention relates to methods of improving cognitive functions, and more particularly, but not exclusively, to methods of improving cognitive functions utilizing compositions which include a GABA agonist moiety, e.g., GABA agonist moiety capable of crossing the blood-brain barrier (BBB).

A series of conjugates of psychotropic drugs and GABA agonists and their use in the treatment of psychotropic and/or proliferative diseases and disorders are described in detail in International Patent Applications published as WO 03/026563 and WO 2005/092392 and in U.S. Patent Application No. 20040242570, which are all incorporated by reference as if fully set forth herein. These conjugates may exert greater therapeutic efficacy and/or cause fewer and/or less severe side effects than their respective non-conjugated psychotropic drugs.

WO 2008/010222 describes novel compositions composed of GABA agonists conjugated to CNS-acting analgesic drugs capable of crossing the BBB.

WO 2008/010222 describes conjugates of anti-parkinsonian drugs such as L-DOPA and GABA agonists and their use in treating neurodegenerative diseases.

SUMMARY OF THE INVENTION

Disclosed herein is a method of improving a cognitive function. The method is achieved by administering to a subject in need thereof a conjugate including a first moiety having GABA agonist activity and a second moiety having CNS activity being covalently linked to the first moiety.

In some embodiments, the conjugate is administered to the subject in an amount effective for improving a cognitive function.

According to some embodiments, the subject has a cognitive impairment or dysfunction. In a further aspect of this embodiment, the subject is afflicted with a disease or disorder selected from the group consisting of a bipolar disorder, Alzheimer's disease, Huntington's disease, dementia, age-related cognitive decline, mild cognitive impairment, multiple sclerosis, Parkinson's disease, stroke, epilepsy, brain injury, chronic fatigue syndrome, fibromyalgia syndrome, memory loss, a memory deficit, a memory deficit related to brain injury or a post-stroke event, a learning deficiency, cognitive impairment associated with schizophrenia, psychosis, attention deficit disorder (ADHD), mood and affective disorders, amyotrophic lateral sclerosis, borderline personality disorder, behavioral and cognitive problems associated with brain tumors, AIDS dementia complex, dementia associated with Down's syndrome, dementia associated with Lewy Bodies, depression, general anxiety disorder, Tourette's syndrome, TNF-α related conditions, rheumatoid arthritis, rheumatoid spondylitis, muscle degeneration, Paget's disease, gouty arthritis, inflammatory bowel disease, adult respiratory distress syndrome (ARDS), Crohn's disease, rhinitis, ulcerative colitis, anaphylaxis, asthma, Reiter's syndrome, tissue and mental retardation.

According to some embodiments of the invention, the subject is afflicted with a disease or disorder selected from the group consisting of age-related cognitive decline, Mild Cognitive Impairment, multiple sclerosis, stroke, brain injury, chronic fatigue syndrome, fibromyalgia syndrome, memory loss, a memory deficit, a memory deficit related to brain injury or a post-stroke event and a learning deficiency.

According to some embodiments, the subject is treated with a CNS-acting drug and is identified, following treatment with said CNS-acting drug, as having a cognitive impairment or dysfunction.

According to an aspect of some embodiments of the present invention there is provided a method of preventing onset or inhibiting progression of a cognitive impairment or dysfunction. The method is achieved by administering to a subject in need thereof a conjugate including a first moiety having GABA agonist activity and a second moiety having CNS activity covalently linked to the first moiety, wherein the conjugate is administered to the subject in an amount effective for preventing onset or inhibiting progression of the cognitive impairment or dysfunction in the subject.

According to some embodiments of the invention, the subject is prone or predisposed to have a cognitive impairment or dysfunction.

According to some embodiments, the subject has been diagnosed for having a disease or disorder selected from the group consisting of a bipolar disorder, Alzheimer's disease, cognitive impairment associated with schizophrenia, Huntington's disease, multiple sclerosis, Parkinson's disease and epilepsy.

According to an aspect of some embodiments of the present invention there is provided an article-of-manufacture. The article-of-manufacture includes a conjugate comprising a first moiety having GABA agonist activity and a second moiety having CNS activity being covalently linked to the first moiety, being packaged in a packaging material and identified in print, on or in the packaging material, for use in improving a cognitive function or for preventing onset or inhibiting progression of a cognitive impairment or dysfunction.

According to some embodiments of the invention, the article-of-manufacturing is identified for use in improving a cognitive function is a subject identified as having a cognitive impairment or dysfunction.

According to some embodiments, the subject is identified as having cognitive impairment or dysfunction following a treatment with a CNS-acting drug.

According to an aspect of some embodiments of the present invention there is provided a method of improving a cognitive function of a subject in need thereof, the method comprising:

(a) performing an evaluation of the cognitive parameters of the subject to thereby determine if the subject is in need for improving a cognitive function; and (b) administering to a subject in need for improving a cognitive function a conjugate including a first moiety having GABA agonist activity and a second moiety having CNS activity being covalently linked to the first moiety, or a pharmaceutically acceptable salt of the conjugate, thereby improving the cognitive function of the subject in need thereof.

According to some embodiments, the subject has a CNS disease or disorder, and is treated with a CNS-acting drug, and wherein performing said evaluation is effected following treatment with said CNS-acting drug.

According to some embodiments, the subject has a family history of schizophrenia or other psychiatric disorder and such evaluation is done before symptoms of schizophrenia or other psychiatric disorders appear.

According to some embodiments, the conjugate is administered to the subject in need for improving a cognitive function in combination with said CNS-acting drug.

According to some embodiments, the conjugate is administered to the subject in need for improving a cognitive function instead of said CNS-acting drug.

According to some embodiments, the CNS-acting drug is said conjugate, and wherein administering said conjugate following said evaluation comprises administering said conjugate using a dosage and regimen sufficient to improve a cognitive function of the subject.

According to some embodiments of the invention, in any of the aspects described herein a pharmaceutically acceptable salt of the conjugate is used.

According to some embodiments of the invention, the conjugate is perphenazine 4-aminobutyrate or a salt thereof (e.g., a trimesylate salt or trihydrochloride salt thereof).

According to an aspect of some embodiments of the invention, there is provided a method for treating a cognitive impairment associated with schizophrenia. The method includes administering to a subject in need thereof an effective amount of a conjugate including a first moiety having GABA agonist activity and a second moiety having CNS activity being covalently linked to the first moiety or a pharmaceutically acceptable salt of the conjugate thereby improving the cognitive function.

According to some embodiments, the conjugate is perphenazine 4-aminobutyrate or a pharmaceutically acceptable salt thereof.

According to some embodiments, the conjugate is tri-mesylate salt or tri-hydrochloride salt of perphenazine 4-aminobutyrate.

According to some embodiments, the conjugate is dosed once daily, e.g., given at a dose of about 25 mg to about 35 mg per day.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be limiting.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DESCRIPTION OF THE PREFERRED EMBODIMENTS

Figure 1:
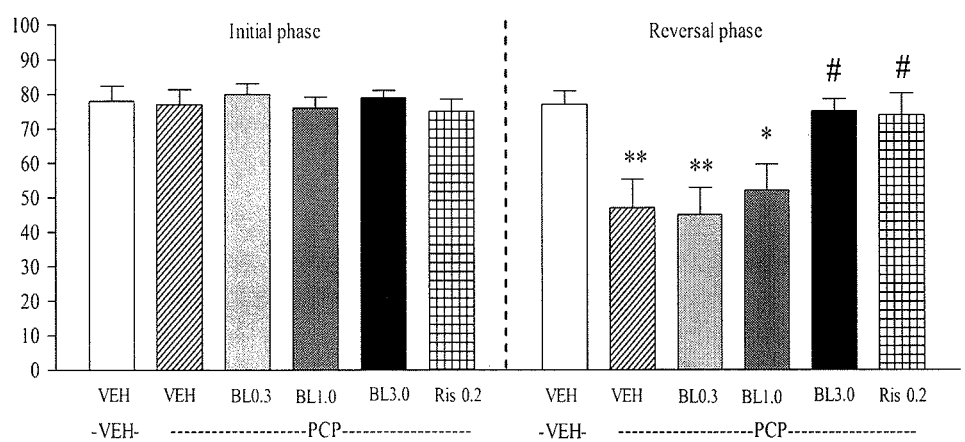
FIG. 1 is a bar chart illustrating the effect of administrating BL-1020 (0.3, 1 and 3 mg/kg) and risperidone (0.2 mg/kg) on the percent correct response (pressing the correct lever) in the PCP-induced reversal learning task. Data are expressed as mean±SEM. Significant differences between drug-treated and vehicle-untreated (not PCP-induced; clear bar) groups are marked by "*" ($P<0.05$) and "**" ($P<0.01$); significant differences between drug-treated groups and untreated (PCP-induced; striped bar) are marked by "#" ($P<0.05$) based on ANOVA followed by Dunnett's t-test.

The present invention relates to methods of improving cognitive functions, and more particularly, but not exclusively, to methods of improving cognitive functions utilizing compositions which include a GABA agonist moiety, e.g., GABA agonist moiety capable of crossing the blood-brain barrier (BBB).

The principles and operation of the present invention may be better understood with reference to the drawings and accompanying descriptions.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Disclosed herein is the discovery that administering a perphenazine-GABA conjugate, (perphenazine 4-aminobutyrate; hereinafter referred to as "BL-1020") to rats having a chemically-induced cognitive deficit resulted in a significant improvement in their cognitive functions ($p<0.01$), while an equal dose of perphenazine alone failed to improve cognitive functions. This result is not observed when $GABA_A$ antagonists are administered prior to administering BL-1020 (see Example 1).

Disclosed herein is the discovery that administering BL-1020 to schizophrenic patients in a human clinical trial significantly improved their cognitive functions as compared to the placebo (p=0.009). In contrast, risperidone (reference antipsychotic drug) failed to improve cognitive functions as compared to the placebo (see Example 2).

Thus, according to one aspect of the present invention there is provided a method of improving a cognitive function. The method is effected by administering to a subject in need thereof a conjugate including a first moiety having GABA agonist activity and a second moiety having CNS activity being covalently linked to the first moiety, or a pharmaceutically acceptable salt of the conjugate.

The phrase "CNS activity" as used herein describes a pharmacological activity exerted in the CNS, which is aimed at treating a CNS-associated impairment. Such a pharmacological activity typically includes modulation of neuronal signals transduction.

A CNS activity therefore includes, without limitation, an anti-psychotic activity, an anti-depression activity, an anti-convulsion activity, or an anti-anxiety activity.

A moiety having CNS activity therefore describes agents capable of (i) crossing the blood-brain barrier (BBB), (ii) acting on the central nervous system (CNS) and (iii) exerting a therapeutic activity in the CNS (exerting a CNS activity).

A moiety having a CNS activity, according to some embodiments of the invention, is therefore derived from a CNS-acting drug. By "derived" it is meant that the moiety was formed upon conjugating the CNS-acting drug, or a derivative thereof, to the first moiety.

The phrase "CNS-acting drug" is also referred to herein interchangeably as "CNS-acting agent".

According to some embodiments, the CNS-acting agent is a psychotropic drug.

Psychotropic drugs are known in the art, and are referred to herein, as pharmacological agents that exert activity in the CNS to thereby treat a CNS-associated disease or disorder.

Psychotropic drugs include, but are not limited to, anti-psychotic drugs (typical and atypical), anxiolytic drugs, anti-depressants, anti-convulsive drugs (also referred to herein and is the art and anti-convulsants), anti-parkinsonian drugs, acetylcholine esterase inhibitors, MAO inhibitors, selective serotonin reuptake inhibitors (SSRIs) and selective noradrenalin receptor inhibitors (SNRIs).

A suitable CNS-acting drug can be, for example, an anxiolytic drug such as, but not limited to, benzodiazepines, phenothiazines and butyrophenones, an MAO inhibitor, an anti-depressant, an anti-convulsant, an anti-parkinsonian drug, an analgesic and an acetylcholine esterase inhibitor. The CNS-acting drug can be tricyclic, bicyclic or monocyclic.

Representative examples of such CNS-acting drugs, include, but are not limited to, perphenazine, chlorpromazine, fluphenazine, zuclopenthixol, thiopropazate, haloperidol, benperidol, bromperidol, droperidol, spiperone, pimozide, piperacetazine, amilsulpride, sulpiride, clothiapine, ziprasidone, remoxipride, sultopride, alizapride, nemonapride, clozapine, olanzapine, ziprasidone, sertindole, quetiapine, fluoxetine, fluvoxamine, desipramine, paroxetine, sertraline, valproic acid, temazepam, flutemazepam, doxefazepam, oxazepam, lorazepam, lormetazepam, cinolazepam, flutazolam, lopirazepam, meprobamate, carisoprodol, acetophenazine, carphenazine, dixyrazine, priciazine, pipothiazine, homophenazine, perimetazine, perthipentyl, flupentixol, piflutixol, teflutixol, oxypethepin, trifluperidol, penfluridol, meclobemide, norclomipramine, amoxapine, nortriptyline, protriptyline, reboxetine, tacrine, rasagiline, amatadine, phenobarbital and phenyloin.

Additional suitable CNS-acting drugs are described in WO 2005/092392, WO 2008/010222 and WO 2009/101616, which are incorporated herein by reference.

In some embodiments, the CNS-acting drug is an anti-psychotic drug such as a phenothiazine (e.g., perphenazine, chlorpromazine, fluphenazine, pipothiazine, acetophenazine, cerphenazine, etc.).

In one embodiment, the CNS-acting drug is perphenazine.

The phrase "GABA agonist" used herein encompasses compounds which are capable of activating the γ-aminobutyric acid system in the brain, either directly or indirectly, including compounds that directly bind the GABA receptor or to any other receptor that affects the GABA system, and are therefore pharmacologically related to GABA.

A suitable GABA agonist can be, for example, γ-aminobutyric acid (GABA), γ-hydroxybutyric acid, baclofen, isonipecotic acid, aminooxyacetic acid, β-(4-chlorophenyl)-γ-aminobutyric acid, piperidine-4-sulfonic acid, 3-aminopropylphosphonous acid, 3-aminopropylphosphinic acid, 3-(aminopropyl)methylphosphinic acid, 1-(aminomethyl)cyclohexaneacetic acid, gabapentin, 4-amino-5-hexenoic acid γ-vinyl GABA (vigabatrin) and 3-(2-imidazolyl)-4-aminobutanoic acid.

Additional suitable GABA agonists are described in WO 2005/092392, WO 2008/010222 and WO 2009/101616, which are incorporated herein by reference as if fully set forth herein.

In one embodiment, the GABA agonist is γ-aminobutyric acid (GABA).

A moiety having GABA agonist activity, according to some embodiments of the invention, is to be regarded as a moiety derived from a GABA agonist as described herein.

By "derived" it is meant that the moiety was formed upon conjugating the GABA agonist, or a derivative thereof, to the second moiety.

The conjugate of the present embodiments includes a GABA agonist (being the first moiety) and a CNS-acting agent (being the second moiety), whereby the first and second moieties are covalently attached to one another thereby forming the conjugate. Each of the conjugates described herein therefore comprises the first moiety (GABA agonist) and a second moiety (a CNS-acting agent or drug) covalently linked to the first moiety.

In some embodiments, the first and second moieties are attached to one another via a covalent bond that is selected or designed capable of dissociating following crossing the BBB.

Thus, the covalent bond linking the first and the second moieties can be selected or designed such that it is not susceptible to dissociation (e.g., by enzymatic reactions) in the periphery and hence the conjugate remains substantially intact before crossing the BBB.

A suitable bond can be, for example, a carboxylic ester bond, an oxyalkyl carboxylic ester bond, an amide bond, a thioester bond, a glycoside bond, a carbonate bond, a carbamate bond, a thiocarbamate bond, an imine bond, a urea bond or a thiourea bond.

As used herein, a "carboxylic ester bond" describes an "—O—C(=O)—" bond.

As used herein, an "oxyalkyl carboxylic ester bond" describes an "O—R—O—C(=O)—" bond, where R is an alkylene, as defined hereinabove. Preferably R is any alkylene other than methylene.

An "amide bond" describes a "—NR'—C(=O)—" bond, where R' is hydrogen, alkyl, cycloalkyl or aryl, as defined herein.

A "thioester bond" describes a "—SR'—C(=O)—" bond, where R' is as defined herein.

A "glycoside bond" describes a —R—O—R— bond, where each R can independently be alkylene, preferably methylene, or absent.

A "carbonate bond" describes a —C(=O)— bond.

A "carbamate bond" describes a —O—C(=O)—NR'— bond, where R' is as defined herein.

A "thiocarbamate bond" describes a —O—C(=S)—NR'— bond, where R' is as defined herein.

A "urea bond" describes a —NR"C(=O)—NR'— bond, where R' is as defined herein and R" is as defined herein for R'.

A "thiourea bond" describes a —NR'—C(=S)—NR" bond, with R' and R" as defined herein.

As used herein, the term "imine bond" describes a —C=NH— bond. An imine bond is also known in the art as a "Schiff base".

As used herein, the term "alkyl" describes a saturated aliphatic hydrocarbon chain including straight chain and branched chain groups. Preferably, the alkyl group has 1 to 20 carbon atoms. Whenever a numerical range, e.g., "1-20", is stated herein, it means that the group, in this case the alkyl group, may contain 1 carbon atom, 2 carbon atoms, 3 carbon atoms, etc., up to and including 20 carbon atoms. More preferably, the alkyl is a medium size alkyl having 1 to 10 carbon atoms. Most preferably, the alkyl has 1 to 5 carbon atoms.

The term "alkylene" describes an alkyl group that is linked to two other groups. Thus, the term ethylene, for example, describes a —CH$_2$CH$_2$— group.

As used herein, the term "cycloalkyl" describes an all-carbon monocyclic or fused ring (i.e., rings which share an adjacent pair of carbon atoms) group wherein one of more of the rings does not have a completely conjugated pi-electron system. Examples, without limitation, of cycloalkyl groups include cyclopropane, cyclobutane, cyclopentane, cyclopentene, cyclohexane, cyclohexadiene, cycloheptane, cycloheptatriene and adamantane.

As used herein, the term "aryl" describes an all-carbon monocyclic or fused-ring polycyclic (i.e., rings which share adjacent pairs of carbon atoms) groups having a completely conjugated pi-electron system. Examples, without limitation, of aryl groups include phenyl, naphthalenyl and anthracenyl.

In some embodiments the bond is an ester bond. As used herein throughout, the phrase "ester bond" encompasses any bond that includes a carboxy (C=O) or a thiocarboxy (C=S) group, such as, for example, a carboxylic ester bond, an oxyalkyl carboxylic ester bond, an amide bond, and a thioester bond, as these are defined herein. In one embodiment the bond is a carboxylic ester bond.

Other bonds, linking the residues of the first and the second moieties, as described hereinabove, can be readily formed by reacting appropriate functional groups of each of the first and the second moieties or derivatives thereof. Thus, for example, a carbamate bond can be formed by reacting an isocyanate and an alcohol, a thiocarbamate bond can be formed by reacting a isothiocyanate and an alcohol, a urea bond can be formed by reacting an isocyanate and an amine, a thiourea bond can be formed by reacting a isothiocyanate and an amine, and an imine bond can be formed by reacting an aldehyde and an amine.

The term "free carboxylic acid" describes a —C(=O)—OH group, ether as is, in its protonated or in its ionized or salt state.

The term "amine" is used herein to describe a —NR'R" group, where R' and R" can be, for example, hydrogen, alkyl, cycloalkyl or aryl, as these terms are defined herein.

The term "halide" and "halo" describes fluorine, chlorine, bromine or iodine.

The term "haloalkyl" describes an alkyl group as defined above, further substituted by one or more halide(s).

The term "ester" describes a —C(=O)—O—R group, where R is alkyl, cycloalkyl or aryl.

The term "haloalkyl ester" describes a —C(=O)—O—R group, where R is a haloalkyl group as defined herein.

The term "aldehyde" describes a —C(=O)—H group.

The term "hydroxyl" describes a —OH group.

The term "alkoxy" describes both an —O-alkyl and an —O-cycloalkyl group, as defined herein.

The term "aryloxy" describes both an —O-aryl and an —O-heteroaryl group, as defined herein.

The term "thiohydroxy" or "thiol" describes a —SH group.

The term "thioalkoxy" describes both a —S-alkyl group, and a —S-cycloalkyl group, as defined herein.

The term "thioaryloxy" describes both a —S-aryl and a —S-heteroaryl group, as defined herein.

The term "isocyanate" describes an —N=C=O group.

The term "isothiocyanate" describes an —N=C=S group.

The term "acyl halide" describes a —(C=O)R"" group wherein R"" is halide, as defined hereinabove.

In one embodiment, the conjugate is perphenazine 4-aminobutyrate (4-amino-butyric acid 2-{4-[3-(2-chloro-phenothiazin-10-yl)-propyl]piperazin-1-yl}-ethyl ester) having the formula

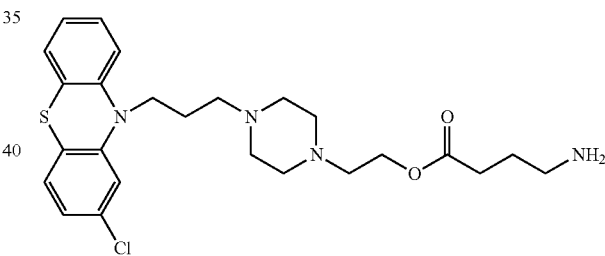

The present embodiments further encompass any pharmaceutically acceptable salt, solvate or hydrate of the conjugates described herein, as well as processes of preparing these pharmaceutically acceptable salts, solvates and hydrates.

The phrase "pharmaceutically acceptable salt" refers to a charged species of the parent compound and its counter ion, which is typically used to modify the solubility characteristics of the parent compound and/or to reduce any significant irritation to an organism by the parent compound, while not abrogating the biological activity and properties of the administered compound (herein, the conjugate). For example, a pharmaceutically acceptable salt of a compound having an amine group can be an acid addition salt. Exemplary acid addition salts suitable for use in some embodiments of the invention include, but are not limited to, hydrochloric acid salt, acetic acid addition salt, ascorbic acid addition salt, benzenesulfonic acid addition salt, camphorsulfonic acid addition salt, citric acid addition salt, maleic acid addition salt, methanesulfonic acid addition salt (mesylate salt), naphthalenesulfonic acid addition salt, oxalic acid addition salt, phosphoric acid addition salt, succinic acid addition salt, sulfuric acid addition salt, tartaric acid addition salt, and toluenesulfonic acid addition salt, each being a mono-acid salt, a di-acid salt or a tri-acid salt.

The term "solvate" refers to a complex of variable stoichiometry (e.g., di-, tri-, tetra-, penta-, hexa-, and so on), which is formed by a solute (the conjugate) and a solvent, whereby the solvent does not interfere with the biological activity of the solute. Suitable solvents include, for example, ethanol, acetic acid and the like.

The term "hydrate" refers to a solvate, as defined hereinabove, where the solvent is water.

The present invention further encompasses various crystalline forms (polymorphs) of the conjugates described herein, as well as processes of preparing these crystalline forms.

In another embodiment the conjugate is a salt of perphenazine 4-aminobutyrate.

In still another embodiment the conjugate is the trimesylate salt or tri-hydrochloride salt of perphenazine 4-aminobutyrate.

Additional suitable conjugates are described in WO 2005/092392, WO 2008/010222 and WO 2009/101616, which are incorporated herein by reference.

The conjugates presented herein can be readily prepared by coupling any GABA agonist and any CNS-acting agent, to thereby obtain a conjugate comprising the first and second linked therebetween. The nature of the bond linking the moieties is typically in accordance with the chemical nature of the second moiety. The chemical nature of the second moiety can be determined by the chemical nature of the CNS-acting agent selected for composing the conjugate.

GABA agonists typically have a free carboxylic acid group, as defined herein. Hence, the process used to prepare the conjugates described herein typically includes reacting a GABA agonist, having a tree carboxylic group, with a CNS-acting drug or a derivative thereof that has a functional group that readily reacts with a carboxylic acid group. In some embodiments, the free carboxylic acid group is activated, prior to the reaction. Such activation includes, for example, converting the free carboxylic group to an acyl halide, and acyl imidazolide, a mixed anhydride, or any of the acyl activating groups suitable for coupling with an alcohol derivative thereof.

Alternatively, various derivatives of the selected CNS-acting drugs and/or the selected GABA agonists, having other functional groups, can be utilized in the process, so as to form conjugates in which the first and the second moieties are linked to one another via other bonds, as is delineated herein.

In cases where the first moiety and the second moiety are linked via a thioester bond, the process of preparing the conjugates described herein is preferably achieved by converting a second compound into its corresponding thiol derivative and converting the first compound into its corresponding acyl chloride derivative, or into any other activated derivative thereof. The thiol derivative is thereafter reacted with the activated first compound, by well-known procedures, so as to obtain the desired conjugate having the first moiety covalently linked to the second moiety via a thioester bond. It should be noted that in cases where the CNS-acting drug includes a free thiol group, it can be directly reacted with an acyl chloride derivative of the first moiety. CNS-acting drugs which do not include a free thiol group can be easily reacted so as to obtain a thiol derivative thereof, by methods well known in the art.

In cases where the first moiety and the second moiety are linked via an amide bond, the process of preparing the conjugates presented herein is achieved, for example, by first converting the first moiety into its corresponding acyl chloride derivative, so as to activate the first moiety and by further converting the second moiety into an amine derivative thereof. The acyl chloride derivative is thereafter reacted with the amino group of the second moiety, in a well-known nucleophilic-addition reaction, or by any other of the known procedures for producing an amide bond, so as to obtain the desired conjugate having the first moiety covalently linked to the second moiety via an amide bond. It should be noted that some CNS-acting drugs include a free amine group and therefore such drugs can be directly reacted with an activated acyl chloride derivative of the first moiety. CNS-acting drugs which do not include a free amine group can be easily reacted so as to obtain an amine derivative thereof, by methods well-known in the art.

In cases where the first moiety and the second moiety are linked via an alkyloxy carboxylic ester bond, the process of preparing the conjugates presented herein is achieved, for example, by converting the second moiety into a chloroalkyl ester derivative thereof. The chloroalkyl ester derivative is thereafter reacted with the first moiety, in a well-known nucleophilic-addition reaction, or by any other of the known procedures for producing an alkyloxy carboxylic ester bond, so as to obtain the desired conjugate having the first moiety covalently linked to the second moiety via an alkyloxy carboxylic ester bond. It should be rioted that covalently linking the first moiety and the second moiety via an alkyloxy carboxylic ester bond is particularly useful in cases where the second moiety includes a free carboxylic acid group, since it avoids the formation of the typically unstable anhydride conjugate.

In cases where the GABA agonist further has a free amine group, in any of the processes described hereinabove, in some embodiments, the amine group is protected during the described reaction with the second moiety. Protecting the free amino group is required since it is a relatively chemically active group, which can therefore undesirably participate in the reaction. Protecting the amine group can be performed by reacting the GABA agonist with a known amine-protecting group such as tert-butoxycarbonyl (Boc) and benzyloxycarbonyl (Cbz). The amino-protected GABA agonist is then reacted with the CNS-acting drug, so as to obtain an amino-protected moiety of the GABA agonist covalently linked to the second moiety. Once the reaction is completed, the protecting group can be removed.

Synthesis of perphenazine 4-aminobutyrate, as well as other exemplary conjugates is described in details in WO 2005/092392, which is incorporated by reference herein as if fully set forth herein.

The preparation of the tri-mesylate salt of perphenazine 4-aminobutyrate is described in Nudelman et al., J. Med. Chem (2008) 51:2858-2862, which is incorporated by reference herein in its entirety.

As is mentioned hereinabove, the conjugate of the present embodiments is capable of improving a cognitive function in a subject. The phrase "cognitive function" used herein refers to any cognitive or mental process or function, including, but not limited to, knowing, thinking, learning, perception, memory, orientation and judging.

The conjugate of the present embodiments may be administered to any subject who needs or elects to improve one or more cognitive functions. The term "subject" used herein refers to a mammal, preferably a human.

The subject can be, but is not limited to, a subject having a cognitive impairment or dysfunction.

In one embodiment, the subject has a cognitive impairment or dysfunction which is associated with a CNS disease or disorder, and the subject is afflicted with the CNS disease or disorder.

Exemplary disease and disorders include, without limitation, a bipolar disorder, Alzheimer's disease, Huntington's disease, dementia, age-related cognitive decline, mild cognitive impairment, multiple sclerosis, Parkinson's disease, stroke, epilepsy, brain injury, chronic fatigue syndrome, fibromyalgia syndrome, memory loss, a memory deficit, a memory deficit related to brain injury or a post-stroke event, a learning deficiency cognitive impairment associated with schizophrenia, psychosis, attention deficit disorder (ADHD), mood and affective disorders, amyotrophic lateral sclerosis, borderline personality disorder, behavioral and cognitive problems associated with brain tumors, AIDS dementia complex, dementia associated with Down's syndrome, dementia associated with Lewy Bodies, depression, general anxiety disorder, Tourette's syndrome, TNF-α related conditions, rheumatoid arthritis, rheumatoid spondylitis, muscle degeneration, Paget's disease, gouty arthritis, inflammatory bowel disease, adult respiratory distress syndrome (ARDS). Crohn's disease, rhinitis, ulcerative colitis, anaphylaxis, asthma, Reiter's syndrome, tissue and mental retardation.

In some embodiments, the subject is diagnosed with Schizophrenia and has cognitive impairment or dysfunction, e.g., has the type of Schizophrenia that involves cognitive impairment such as disorganized type or undifferentiated type of schizophrenia.

In some embodiments, the subject is diagnosed with Schizophrenia and has cognitive impairment or dysfunction and is treated at the onset or in the duration of Schizophrenia with a conjugate of perphenazine 4-aminobutyrate or a pharmaceutically acceptable salt thereof to prevent, improve, and/or delay cognitive impairment or dysfunction associated with Schizophrenia.

In some embodiments, the subject is afflicted with a disease or disorder selected from the group consisting of age-related cognitive decline, mild cognitive impairment, multiple sclerosis, stroke, brain injury, chronic fatigue syndrome, fibromyalgia syndrome, memory loss, a memory deficit, a memory deficit related to brain injury or a post-stroke event, and a learning deficiency.

In some embodiments, the method as described herein utilizes the conjugates as described herein for treating a subject afflicted with a CNS disease or disorder associated with a cognitive impairment or dysfunction, whereby the moiety having a CNS activity is derived from a CNS-acting drug that is typically not used for treating the CNS disease or disorder associated with the cognitive impairment or dysfunction.

For example, according to some embodiments of the present invention, a conjugate comprising as a second moiety a CNS-acting drug useful in treating Schizophrenia (e.g., perphenazine) is used in a method of treating a subject afflicted with a CNS disease or disorder other than Schizophrenia.

Thus, embodiments of the invention encompass any combination of a moiety having a CNS activity in the conjugate and a subject afflicted by a disease or disorder that is treatable by such a conjugate, which is not described in WO 2005/092392, WO 2008/010222 and WO 2009/101616.

It is to be noted that any method that utilizes a conjugate as described herein, in which the second moiety is a CNS-acting drug, wherein the conjugate is administered to a subject afflicted by a disease or disorder that has been described in any of WO 2005/092392, WO 2008/010222 and WO 2009/101616, as treatable by a conjugate that comprises this CNS-acting drug, is excluded from the scope of embodiments of this aspect of the invention, unless otherwise indicated herein. Thus, any combination of a CNS-acting drug as a second moiety in a conjugate and a CNS disease or disorder described as treatable by such a conjugate, which has been described in any of WO 2005/092392, WO 2008/010222 and WO 2009/101616, is excluded from the scope of some embodiments of this aspect of the invention, unless otherwise indicated herein.

In some embodiments, the subject is not afflicted with Schizophrenia.

Alternatively, the subject is afflicted with Schizophrenia and the method is achieved by administering the conjugate to the subject in a dosage and regimen effective for improving a cognitive function in the subject, whereby the dosage and regimen are different from the therapeutically effective dosage and regimen required for treating Schizophrenia but without improving the cognitive function of the subject.

In some embodiments, in any of the methods described herein, the conjugate is administered in an amount (e.g., dosage and regimen) effective for improving a cognitive function in the subject.

The phrase "an amount effective for improving cognitive function" used herein refers to an amount (e.g., dosage and regimen) of conjugate which can exert a detectable improvement in a cognitive function. Assessment of baseline cognitive functions in a subject and improvement thereof can be determined by using various tests known in the art such as, for example, the Rey Auditory Verbal Learning Test (RAVLT); Cambridge Neuropsychological Test Automated Battery (CANTAB); a Children's Memory Scale (CMS); a Contextual Memory Test; a Continuous Recognition Memory Test (CMRT); a Denman Neuropsychology Memory Scale; a Fuld Object Memory Evaluation (FOME); a Graham-Kendall Memory for Designs Test; a Guild Memory Test; a Learning and Memory Battery (LAMB); a Memory Assessment Clinic Self-Rating Scale (MAC-S); a Memory Assessment Scales (MAS); a Randt Memory Test; a Recognition Memory Test (RMT); a Rivermead Behavioral Memory Test; a Russell's Version of the Wechsler Memory Scale (RWMS); a Test of Memory and Learning (TOMAL); a Vermont Memory Scale (VMS); a Wechsler Memory Scale; a Wide Range Assessment of Memory and Learning (WRAML); First-Last Name Association (Youngjohn J. R., et al., Archives of Clinical Neuropsychology 6:287-300, 1991); Name-Face Association; Wechsler Memory Scale-Revised (Wechsler, D., Wechsler Memory Scale-Revised Manual, NY, N.Y., The Psychological Corp 1987) California Verbal Learning Test-Second Edition (Delis, D. C., et. al., The Californian Verbal Learning Test, Second Edition, Adult Version, Manual, San Antonio, Tex.: The Psychological Corporation, 2000); Facial Recognition (delayed non-matching to sample); Cognitive Drug Research (CDR) Computerized Assessment Battery-Wesnes; Buschke's Selective Reminder Test (Buschke, H., et al., Neurology 24: 1019-1025, 1974); Telephone Dialing Test; Brief Visuospatial Memory Test-Revised; and Test of Everyday Attention (Perry, R. J., et al., Neuropsychologia 38: 252-271, 2000); the Wechsler Adult Intelligence Scale (WAIS); the CERAD word list (CWL) test; the Symbol Digit Modalities Test [SDMT; Smith, A. (1982). Symbol Digit Modalities Test. Los Angeles: Western Psychological Services; Smith, A. (1968). The symbol-digit modalities test: a neuropsychologic test of learning and other cerebral disorders. In J. Helmuth (Ed.), Learning disorders (pp. 83-91). Seattle; Special Child Publications]; the Mini-Mental State Exam (MMSE; Folstein, M. F. et al., J. Psych. Res. 12:189-198, 1975); Test of Nonverbal Intelligence and Comprehensive Test of Nonverbal Intelligence (CTONI-2; Donald D. et al., (Eds.) American Therapy Publications, 2009); A Development Neuropsychological Assessment (NEPSY); Delis-Kaplan Executive Function System (D-KEFS); Comprehensive Test of Phonological Processing (CTOPP); Rey-Osterrieth Complex Figure Test; Children's Memory Scale, Wechsler Memory Scale—Third Edition (WMS-III); Woodcock-Johnson Tests of Cognitive Abilities (WJIII); Beery-Buktenica Developmental Test of Visual Motor Integration; Wisconsin Card Sorting Test (WCST); Children's Category Test, Judgment of Line Orientation; Behavior Rating Inventory of Executive Function; and Wide Range Assessment of Memory and Learning (WRAML); and the Stanford-Binet intelligence Scale (SB5; Roid, G. H. (2003) Stanford Binet intelligence scales, 5th Edition, Itasca, Ill.: Riverside Publishing).

Additional procedures which may be used to assess cognitive functions are described in U.S. Pat. Nos. 4,203,452, 5,339,826, 5,447,166 and 6,947,790 and U.S. Patent Application Publication Nos. 20020192624 and 20090155754.

When a subject treated by a conjugate is afflicted by a disease or disorder that is treatable by the conjugate, the phrase "an amount effective for improving cognitive function" can be higher than, lower than or the same as a therapeutically effective amount of the conjugate as determined for the disease or disorder in the subject.

In some embodiments, an amount effective for improving cognitive function in such a subject is higher than a therapeutically effective amount of the conjugate in the subject.

In some embodiments, an amount effective for improving cognitive function in such a subject is lower than a therapeutically effective amount of the conjugate in the subject.

Embodiments according to which an amount effective for improving cognitive function in such a subject is different from a therapeutically effective amount of the conjugate in the subject encompass any combination of a CNS-acting drug in the conjugate and a subject afflicted by a disease or disorder that can be treated by the conjugate.

For example, in some embodiments, a subject is afflicted with Schizophrenia and suffers from a cognitive impairment or dysfunction, and is administered with a conjugate as described herein in such a dosage and regimen effective for improving a cognitive function in the subject, whereby the dosage and regimen result is an amount which is higher than a therapeutically effective amount of the conjugate for treating Schizophrenia in the subject but which does not improve the cognitive function in the subject.

In some other embodiments, a subject has a cognitive impairment or dysfunction associated with Schizophrenia and is administered with a conjugate of perphenazine 4-aminobutyrate or a pharmaceutically acceptable salt thereof in a dosage from about 10 mg to about 100 mg, about 10 mg to about 150 mg, about 10 mg to about 20 mg, about 20 mg to about 30 mg, about 30 mg to about 40 mg, about 40 mg to about 50 mg, about 50 mg to about 60 mg, about 60 mg to about 70 mg, about 70 mg to about 80 mg, about 80 mg to about 90 mg, about 90 mg to about 100 mg.

In some other embodiments, a subject has a cognitive impairment or dysfunction associated with Schizophrenia and is administered with a conjugate of perphenazine 4-aminobutyrate or a pharmaceutically acceptable salt thereof in a dosage from about 25 mg to about 35 mg, about 20 mg to about 25 mg, about 25 mg to about 30 mg, about 30 mg to about 35 mg once daily.

In some embodiments, a subject has a cognitive impairment or dysfunction associated with Schizophrenia and is administered with a conjugate of perphenazine 4-aminobutyrate or a pharmaceutically acceptable salt thereof in an effective amount once daily or once every other day or twice a day.

In some other embodiments, a subject has a cognitive impairment or dysfunction associated with Schizophrenia and is administered with a conjugate of perphenazine 4-aminobutyrate or a pharmaceutically acceptable salt thereof in a dosage from about 25 mg to about 35 mg once daily.

According to another aspect of some embodiments there is provided a method of improving a cognitive function, which is achieved by:

(a) performing an evaluation of the cognitive parameters of the subject to thereby determine if the subject is in need for improving a cognitive function; and (b) administering to a subject in need for improving a cognitive function a conjugate including a first moiety having GABA agonist activity and a second moiety having CNS activity being covalently linked to said first moiety, or a pharmaceutically acceptable salt thereof.

Evaluation of cognitive parameters can be achieved as described herein.

In some embodiments, the subject has a CNS disease or disorder, and is treated with a CNS-acting drug, and, following treatment with the CNS-acting drug, evaluating the cognitive parameters of the subject is effected.

In such cases, subjects identified as being in need for improving a cognitive function, are administered with a conjugate as described herein, either in combination with the CNS-acting drug or as a substituting therapy.

A subject can be identified as being in need for improving a cognitive function in cases where the subject was afflicted with a cognitive impairment or dysfunction associated with the CNS disease or disorder and the CNS-acting drug has proved ineffective in improving one or more cognitive functions. Alternatively, a subject can be identified as being in need for improving a cognitive function in cases where the subject developed a cognitive impairment or dysfunction as a result of progression of the CNS disease or disorder, or as a result of his age.

In some embodiments, the subject is treated with a CNS-acting drug which is a conjugate as described herein, yet was identified in said evaluation as being in need for improving a cognitive function. In these embodiments, administering the conjugate is in a dosage and regimen sufficient to improve a cognitive function of the subject. Typically, the dosage and regimen result in an amount of the conjugate which is higher than used before said evaluation was performed.

Any combination of a subject afflicted by a disease or disorder and a conjugate comprising a CNS-acting drug useful in the treatment of the disease or disorder is encompassed by these embodiments of the invention Exemplary diseases and disorders include, without limitation, psychotic disorders or diseases, anxiety disorders, dissociative disorders, personality disorders, mood disorders, affective disorders, neurodegenerative diseases or disorders, convulsive disorders, boarder line disorders and mental diseases or disorders, as well as dementia, age-related cognitive decline, mild cognitive impairment, multiple sclerosis, Parkinson's disease, stroke, epilepsy, brain injury, chronic fatigue syndrome, fibromyalgia syndrome, memory loss, a memory deficit, a memory deficit related to brain injury or a post-stroke event, a learning, deficiency cognitive impairment associated with schizophrenia, psychosis, attention deficit disorder (ADHD), mood and affective disorders, amyotrophic lateral sclerosis, borderline personality disorder, behavioral and cognitive problems associated with brain tumors, AIDS dementia complex, dementia associated with Down's syndrome, dementia associated with Lewy Bodies, depression, general anxiety disorder, Tourette's syndrome, TNF-α related conditions, rheumatoid arthritis, rheumatoid spondylitis, muscle degeneration, Paget's disease, gouty arthritis, inflammatory bowel disease, adult respiratory distress syndrome (ARDS), Crohn's disease, rhinitis, ulcerative colitis, anaphylaxis, asthma, Reiter's syndrome, tissue and mental retardation.

Exemplary CNS-acting drugs are described herein.

Optionally, the conjugate of the present embodiments may be utilized as a prophylactic treatment for preventing onset or inhibiting progression of a cognitive impairment or dysfunction in a subject prone or predisposed to cognitive impairment or dysfunction. In some embodiments the subject is diagnosed for having a bipolar disorder, Alzheimer's disease, Huntington's disease, multiple sclerosis, Parkinson's disease, brain injury, stroke, age-related disease or disorder or epilepsy.

In some embodiments, the conjugate is administered to the subject in an amount effective for preventing onset or inhibiting progression of the cognitive impairment or dysfunction in the subject.

Assessment of cognitive impairment or dysfunction in a subject and prevention or inhibition thereof can be determined by assessing cognitive functions in the subject, using any of the assays delineated hereinabove.

In some embodiments the subject is a person with a family history of schizophrenia or other psychiatric disorders who is tested for cognitive dysfunction before or as clinical symptoms of schizophrenia or other psychiatric disorders emerge. If a cognitive dysfunction is found such subject is treated with a conjugate described herein.

The conjugate of the present invention can be administered to the subject either per se or as part (active ingredient) of a pharmaceutical composition.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Suitable routes of administration may, for example, include oral, rectal, transmucosal, especially transnasal, intestinal or parenteral delivery, including intramuscular, subcutaneous and intramedullary injections as well as intrathecal, direct intraventricular, intravenous, intraperitoneal, intranasal, or intraocular injections.

Alternately, one may administer the pharmaceutical composition in a local rather than systemic manner, for example, via injection of the pharmaceutical composition directly into a bone tissue region of a patient.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries, which facilitate processing of the active ingredients into preparations which can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. One route of administration which is suited for the pharmaceutical compositions of the present invention is sub-periosteal injection, as described in U.S. Pat. No. 6,525,030 to Erikkson. For transmucosal administration, penetrants appropriate to the barrier to be permeated are used in the formulation. Such penetrants are generally known in the art.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethylcellulose, sodium carbomethylcellulose; and/or physiologically acceptable polymers such as polyvinylpyrrolidone (PVP). If desired, disintegrating agents may be added, such as cross-linked polyvinylpyrrolidone, agar, or alginic acid or a salt thereof such as sodium alginate. As used herein, the term "oral administration" includes administration of the pharmaceutical compound to any oral surface, including the tongue, gums, palate, or other buccal surfaces. Addition methods of oral administration include provision of the pharmaceutical composition in a mist, spray or suspension compatible with tissues of the oral surface.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions, which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients thr use according to the present invention are conveniently delivered in the form of an aerosol spray presentation from a pressurized pack or a nebulizer with the use of a suitable propellant, e.g., dichlorodifluoromethane, trichlorofluoromethane, dichlorotetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The pharmaceutical composition described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow fix the preparation of highly concentrated solutions.

Alternatively, the active ingredient may be in powder form for constitution with a suitable vehicle, e.g., sterile, pyrogen-free water based solution, before use.

The pharmaceutical composition of the present invention may also be formulated in rectal compositions such as suppositories or retention enemas, using, e.g., conventional suppository bases such as cocoa butter or other glycerides.

Pharmaceutical compositions suitable for use in context of the present invention include compositions wherein the active ingredients are contained in an amount effective to achieve the intended purpose. More specifically, a physiologically effective amount means an amount of active ingredients effective to improve a cognitive function in the subject.

Determination of suitable doses is well within the capability of those skilled in the art, especially in light of the detailed disclosure provided herein.

For any preparation used in the methods of the invention, the therapeutic dose can be estimated in an animal model, such as, tar example, the reversal learning task rat model (Abdul-Monim et al., Behav Brain Res. 169: 263-273, 2006; and Abdul-Monim et al., J. Psychopharmacology 21: 198-205, 2007; see Example 1 hereinbelow). Such information can be used to more accurately determine useful doses in humans.

Toxicity and therapeutic efficacy of the active ingredients described herein can be determined by standard pharmaceutical procedures in experimental animals. The data obtained from these animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Dosage amount and interval may be adjusted individually to levels of the active ingredient which are sufficient to cause detectable improvement in cognitive functions (minimal effective concentration, MEC). The MEC will vary for each preparation, but can be estimated from in vivo data. Dosages necessary to achieve the MEC will depend on individual characteristics and route of administration. Detection assays can be used to determine plasma concentrations.

When the subject is afflicted with a disease or disorder associated with cognitive impairment or dysfunction, depending on the severity and responsiveness of the condition to be treated, dosing can be of a single or a plurality of administrations, with course of treatment lasting from several days to several weeks or diminution of the disease state is achieved.

The amount of a composition to be administered will, of course, be dependent on the subject being treated, the severity of the affliction, the manner of administration, the judgment of the prescribing physician, etc.

Compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert.

The conjugate or the pharmaceutical composition of the present invention may be placed in an appropriate container, and identified in print, on or in the packaging material, as an article-of-manufacturing for use in improving cognitive functions or in preventing onset or inhibiting progression of a cognitive impairment or dysfunction, as derailed herein.

According to an aspect of some embodiments of the present invention there is provided a conjugate as described herein, characterized for use in improving a cognitive function is a subject in need thereof, as described herein.

According to an aspect of some embodiments of the present invention there is provided a conjugate as described herein, characterized for use in preventing onset of inhibiting progression of a cognitive impairment or dysfunction.

According to an aspect of some embodiments of the present invention there is provided a conjugate as described herein, characterized for use in improving a cognitive function in a subject identified as being in need for improving a cognitive function upon evaluating cognitive parameters of the subject.

According to an aspect of some embodiments of the present invention there is provided a use of a conjugate as described herein in the preparation of a medicament e.g. a pharmaceutical composition as described herein) for improving a cognitive function, preventing onset of inhibiting progression of a cognitive impairment or dysfunction, and/or for improving a cognitive function in a subject identified as being in need for improving a cognitive function upon evaluating cognitive parameters of the subject.

As used herein the term "about" refers to ±10%.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Example 1

BL-1020 Attenuates PCP-Induced Learning Deficit in Rats

Materials and Methods

Test Agents

Antipsychotic drugs: BL-1020 (perphenazine 4-aminobutyrate, mesylate salt; BioLineRx Ltd., Israel; administered per os); risperidone (Sigma, UK; administered intra-peritoneally); and perphenazine (Sigma, Israel; administered per os).

$GABA_A$ antagonists: picrotoxin (Sigma, UK; administered intra-peritoneally); and bicuculline (Sigma, UK; administered intra-peritoneally).

Animals

Female hooded-Lister rats (Charles River, UK) were housed in groups of five under standard laboratory conditions under a 12 hr diurnal cycle. Rats were maintained at approx 85% of free-feeding body weight average (250 grams) for the duration of the study.

Operant Training Sessions

Following habituation to the operant chambers, rats were trained to respond for food on an FR1 (Fixed Ratio 1) schedule of reinforcement with active levers active, as described by Abdul-Monim et al. (*J. Psychopharmacology* 17: 57-65, 2003). When a proper response for food was established the rats were trained to press either the left or right lever (only one of levers was active) for food delivery. The active lever was varied from day to day using a pseudorandom Gellerman schedule, which randomly assigns either the left or right lever as active, thus avoiding generation of a lever bias. Each session lasted 20 minutes and counts were recorded on each lever.

Following completion of the first phase of training (within about two weeks) the rats were trained to respond ter food according to the position of a visual cue (a lit LED). Half of the rats were trained to press the lever under the lit LED in order to receive a food reward. The other half of the rats were trained on the opposite contingency (i.e., to press the lever under the non-lit LED). Each training session began with illumination of the house-light. After three seconds both levers, together with the visual cue, were presented. The cue was presented for one second. Following a lever press, a correct response resulted in delivery of a food pellet. The levers were then retracted and the house light was extinguished for a three-second time-out period, during which the pellet was consumed (if a correct response had been made). The house-light was then turned on again and the cycle repeated. Following 128 lever presses (which lasted approximately 30 minutes) the training session was terminated.

Each rat had one training session per day. Rats were required to make at least 115 responses on the correct lever (90% correct responding) on at least three consecutive days (which was generally achieved within two weeks). The contingency (visual cue, i.e. LED on or off, relative to active lever) remained constant during this period, though the position of the active lever varied from day to day according to a pseudo-random Gellerman schedule.

Subsequently, rats were trained until they again reached criterion on the opposite contingency (which was generally achieved within two weeks)). Rats achieved criterion at the same rate irrespective of whether they responded to one rule or the other. Following a total of approximately six weeks of habituation and training, the reversal learning task was introduced.

Reversal Learning Task

Prior to performing the reversal learning task rats were injected (2 mg/kg; intra-peritoneally) with phencyclidine hydrochloride (PCP; Sigma, UK; a non-competitive NMDA receptor antagonist; Abdul-Monim et al., Behav Brain Res. 169: 263-273, 2006; and Abdul-Monim et al., *J. Psychopharmacology* 21: 198-205, 2007) twice daily for 7 days.

Following a 7 day drug (PCP)-free period the rats were treated with test agents (antipsychotic drugs and $GABA_A$-receptor antagonists). Sixty minutes later the rats were exposed for five-minutes ("initial phase") to the same contingency (cue position relative to active lever) as was during the operant training session and their responses (pressing on correct and incorrect levers) were recorded. Following a two-minutes recess the animals were exposed for five-minutes to a reversed contingency ("reversal phase") during which their responses (pressing on correct and incorrect levers) were recorded.

Statistical Analysis

Data were analyzed by one way ANOVA followed by post-hoc Dunnett's t-test.

Results

Figure 2:
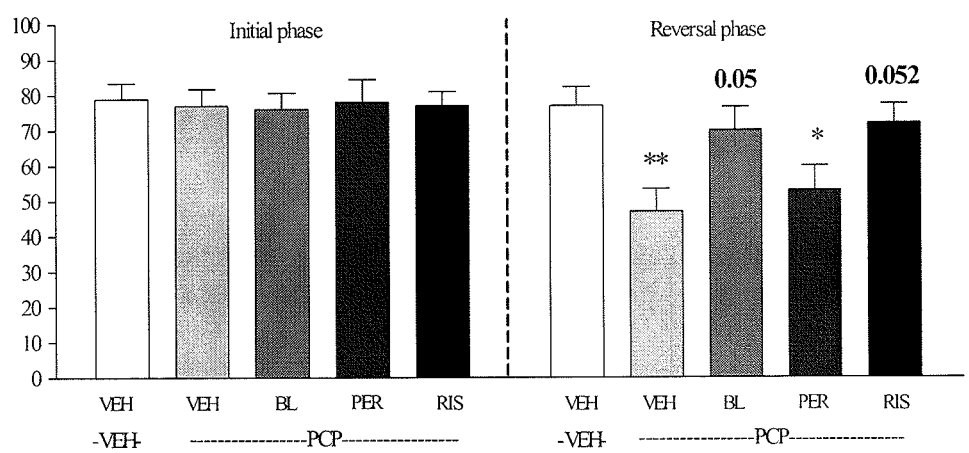
FIG. 2 is a chart illustrating the effect of administrating BL-1020 (3 mg/kg), perphenazine (2.49 mg/kg) and risperidone (0.2 mg/kg) on the percent correct response (pressing the correct lever) in the PCP-induced reversal learning task. Data are expressed as mean±SEM. Significant differences between drug-treated and the vehicle-untreated (not PCP-induced; clear bar) groups are marked by "*" ($P<0.05$) and "**" ($P<0.01$); the numbers "0.05" and "0.052" are p values estimated for the differences between the drug-treated and untreated (PCP-induced; grey bar) groups based on ANOVA followed by Dunnett's t-test.
Figure 3:
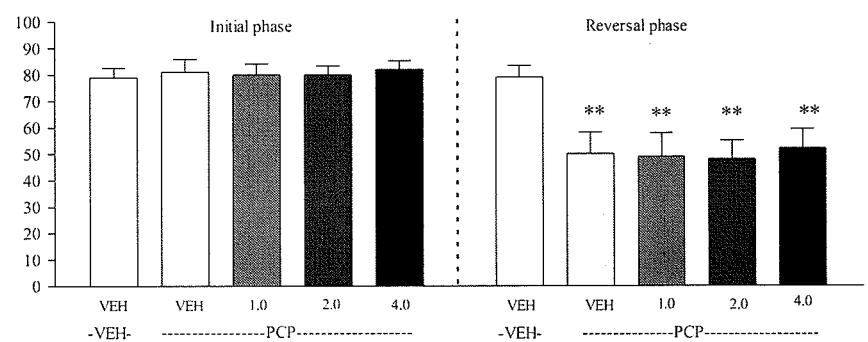
FIG. 3 is bar chart illustrating the effect of administrating bicuculline (1, 2 and 4 mg/kg) on the percent correct response (pressing the correct lever) in the PCP-induced reversal learning task. Data are expressed as mean±SEM. Significant differences between bicuculline-treated and vehicle-treated groups are marked by "**" ($P<0.01$), based on ANOVA followed by Dunnett's t-test.

Phencyclidine hydrochloride (PCP) injected to rats at 2 mg/kg twice daily for 7 days significantly reduced the percent correct responding animals in the reversal learning task (FIGS. 1, 2 and 3; $p<0.01$).

BL-1020 administered at a dose of 3 mg/kg significantly improved the PCP-induced reversal learning deficit (FIGS. 1 and 3; $p<0.01$). In contrast, perphenazine (same CNS-active moiety as BL-1020 but lacking the GABA moiety) administered at a dose of 2.49 mg/kg (which is equivalent to the perphenazine moiety in 3 mg/kg BL-1020 dose) did not significantly improve the PCP-induced reversal learning deficit (FIG. 2).

Figure 4:
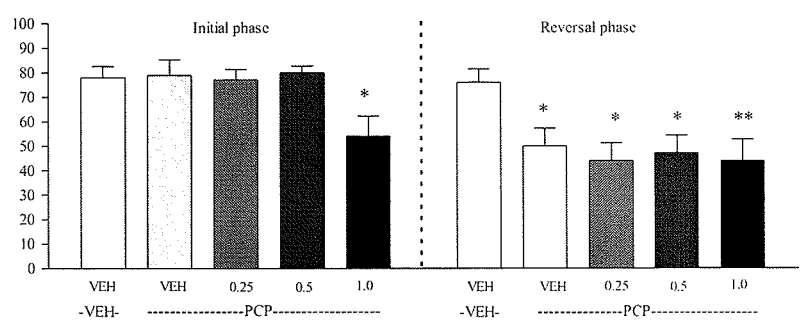
FIG. 4 is bar chart illustrating the effect of administrating picrotoxin (0.25, 0.5 and 1 mg/kg) on the percent correct response (pressing the correct lever) in the PCP-induced reversal learning task. Data are expressed as mean±SEM. Significant differences between picrotoxin-treated and vehicle-treated groups are marked by "*" ($P<0.05$) and "**" ($P<0.01$), based on ANOVA followed by Dunnett's t-test.

$GABA_A$ antagonist bicuculline administered at a dose of 1, 2 and 4 mg/kg did not significantly improve the PCP-induced reversal learning deficit (FIG. 3). Similarly, $GABA_A$ antagonist picrotoxin administered at a dose of 0.25, 0.5 and 1 mg/kg did not significantly improve the PCP-induced reversal learning deficit (FIG. 4).

Figure 5:
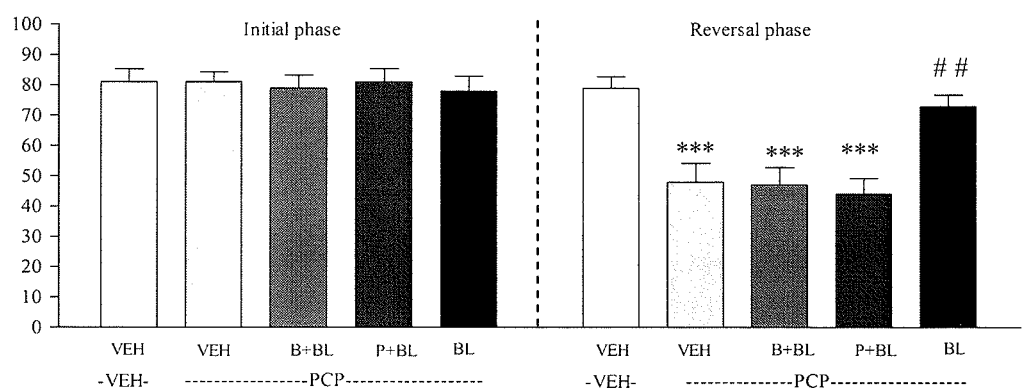
FIG. 5 is bar chart illustrating the effect of administrating BL-1020 (3 mg/kg) alone and combined with bicuculline (2 mg/kg) or picrotoxin (0.5 mg/kg) on the percent correct response (pressing the correct lever) in the PCP-induced reversal learning task. Data are expressed as mean±SEM. Significant differences between agent-treated and the vehicle-untreated (not PCP-induced; clear bar) groups are marked by "***" ($P<0.001$); significant differences between agents-treated and untreated (PCP-induced; grey bar) alone groups are marked by are marked by ## ($P<0.01$) based on ANOVA followed by Dunnett's t-test.

$GABA_A$ antagonists bicuculline (2 mg/kg) and picrotoxin (0.5 mg/kg), co-administered with BL-1020 (3 mg/kg), negated the BL-1020 effect on improving the PCP-induced reversal learning deficit (FIG. 5; p<0.001).

Hence, these results indicate that BL-1020 (a perphenazine-GABA conjugate) is capable of improving learning deficit in rats and that this activity may involve $GABA_A$ receptor activation.

Example 2

BL-1020 Improves Cognitive Functions in Human Patients Having Acute Exacerbation of Schizophrenia Experimental Design The trial was conducted at forty sites located in the USA, Europe and India. For the trial 363 patients were recruited and randomized equally. Drugs (BL-1020, 10 mg/day; BL-1020, 20-30 mg/day; risperidone, 2-8 mg/day and placebo) have been administered to designated patients (double blinded) daily over a period of 42 days.

The study was designed to demonstrate statistically significant superiority of BL-1020 to placebo on the primary efficacy measure, the total score of the Positive and Negative Symptom Scale (PANSS). Key secondary efficacy measures included the Clinical Global Impression of Severity (CGI-S), the Clinical Global Impression of Change (CGI-C) from baseline, and effect on cognition as measured by the Brief Assessment of Cognition in Schizophrenia (BACS). Risperidone at a dose of 2-8 mg was included as a positive control to validate the study results.

Assessment of Cognitive Functions

Assessments of cognitive functions of treated patients have been performed on day zero (baseline) and on day 42 (end of study), using the test battery designed for use in patients with schizophrenia [Richard Keefe (Ed.), Brief Assessment of Cognition in Schizophrenia (BACS) Version 3.0, Duke University Medical Center, 1999; and Keefe et al., *Schizophrenia Research*, 68: 283-297, 2004]. The battery consists of brief assessments of processing speed, reasoning and problem solving and verbal and working memory. A composite score is obtained by summing the z-scores of six measures (verbal memory, digit sequencing, token motor task, fluency, symbol coding and Tower of London).

Results

The mean BACS score values on day 0 (baseline) and the mean BACS score changes after 42 days of treatment are summarized in Table 1 hereinbelow. The Table shows that patients treated with BL-1020 at high dose (20-30 mg/day) exhibited a BACS score increase of 8.3 points, which was significantly superior to patients treated with placebo and risperidone (p-values 0.009 and 0.013 respectively).

Hence, the results clearly indicate that BL-1020 is capable of improving cognitive functions in schizophrenic patients.

TABLE 1

BACS Test Mean Scores at Baseline and Mean Change at Day 42

| Study Day | BL-1020 10 mg/day (n = 90) Mean (SD) | BL-1020 30 mg/day (n = 89) Mean (SD) | Risperidone 8 mg/day (n = 91) Mean (SD) | Placebo (n = 93) Mean (SD) |
|---|---|---|---|---|
| Baseline [a] | 16.7 (15.5) | 15.3 (15.5) | 13.5 (12.3) | 16.5 (15.4) |
| Day 42 [b] | 5.1 (7.1) | 8.3 (8.5) | 5.7 (6.2) | 6.0 (10.0) |
| Statistical Analysis - ANCOVA Model [c] | | | | |
| vs. Placebo | | | | |
| Difference in LS-means | 0.63 | 3.92 | 0.52 | — |
| 95% CI | −2.21, 3.47 | 0.99, 6.85 | −2.29, 3.34 | — |
| P-value | 0.660 | 0.009 | 0.713 | — |
| vs. Risperidone | | | | |
| Difference in LS-mean | 0.11 | 3.40 | — | — |
| 95% CI | −2.51, 2.73 | 0.74, 6.06 | | |
| P-value | 0.935 | 0.013 | | |

SD = standard deviation.
LS-Mean = least squares mean.
95% CI = 95% confidence interval.
[a] Baseline values represent means.
[b] Day 42 values represent mean changes from baseline.
[c] ANCOVA model with treatment, site and baseline value as covariates.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of improving a cognitive function of a subject diagnosed as having schizophrenia, the method comprising:
    (a) performing an evaluation of the cognitive parameters of the subject to thereby determine if the subject is in need for improving a cognitive function; and
    (b) administering to a subject in need for improving a cognitive function a conjugate, said conjugate being perphenazine 4-aminobutyrate or a pharmaceutically acceptable salt thereof,
    said conjugate being administered in a dosage and regimen effective for improving the cognitive function in the subject, said dosage and regimen result is an amount which is higher than a therapeutically effective amount of the conjugate for treating Schizophrenia in the subject,
    thereby improving the cognitive function of the subject.

2. The method of claim 1, wherein the subject is treated with a CNS-acting drug, and wherein performing said evaluation is effected following treatment with said CNS-acting drug.

3. The method of claim 2, wherein said conjugate is administered to the subject in need for improving a cognitive function in combination with said CNS-acting drug.

4. The method of claim 2, wherein said CNS-acting drug is said conjugate, and wherein administering said conjugate following said evaluation comprises administering said conjugate in a higher amount than used before performing said evaluation.

5. The method of claim 3, wherein said conjugate is administered to the subject in need for improving a cognitive function instead of said CNS-acting drug.

6. The method of claim 1, wherein said conjugate is a tri-mesylate salt or tri-hydrochloride salt of said perphenazine 4-aminobutyrate.

7. The method of claim 6, wherein said conjugate is given at a dose of about 25 mg to about 35 mg per day.

8. The method of claim 1, wherein said conjugate is dosed once daily.

9. The method of claim 1, wherein said cognitive function is selected from the group consisting of knowing, thinking, learning, perception, memory, orientation and judging.

* * * * *